(12) United States Patent
Taub

(10) Patent No.: US 6,762,174 B1
(45) Date of Patent: Jul. 13, 2004

(54) LOW MOLECULAR WEIGHT COMPOUNDS ADMINISTERED TOGETHER WITH ANTI-CANCER AGENTS TO PREVENT OR TREAT CANCER AND PHARMACEUTICAL COMPOSITIONS THEREOF

(75) Inventor: Floyd E. Taub, Silver Spring, MD (US)

(73) Assignee: Dovetail Technologies, Inc., College Park, MD (US)

( * ) Notice: Subject to any disclaimer, the term of this patent is extended or adjusted under 35 U.S.C. 154(b) by 0 days.

(21) Appl. No.: 09/256,764

(22) Filed: Feb. 24, 1999

Related U.S. Application Data

(60) Provisional application No. 60/085,474, filed on May 14, 1998, and provisional application No. 60/075,966, filed on Feb. 24, 1998.

(51) Int. Cl.[7] .................... A61K 31/675; A61K 31/66; A61K 31/195; A61K 31/16
(52) U.S. Cl. ..................... 514/90; 514/110; 514/567; 514/626
(58) Field of Search ................. 514/626, 110, 514/449, 567, 90

(56) References Cited

U.S. PATENT DOCUMENTS

| 3,789,125 | A | | 1/1974 | Kuger et al. | |
|---|---|---|---|---|---|
| 4,102,948 | A | | 7/1978 | Feuer et al. | |
| 4,218,404 | A | | 8/1980 | Feuer et al. | |
| 5,578,313 | A | | 11/1996 | Knight et al. | |
| 5,643,966 | A | | 7/1997 | Knight et al. | |
| 6,007,819 | A | * | 12/1999 | Taub et al. | 424/184.1 |
| 6,046,241 | A | * | 4/2000 | Knight et al. | 514/626 |
| 6,166,086 | A | * | 12/2000 | Taub | 514/626 |
| 6,451,853 | B1 | * | 9/2002 | Taub et al. | 514/528 |

FOREIGN PATENT DOCUMENTS

| AU | 655598 | 7/1991 |
|---|---|---|
| EP | 0 538 330 | 10/1995 |
| WO | WO 97/14306 | 4/1997 |

OTHER PUBLICATIONS

Carter et al., Chemotherapy of Cancer, second edition, pp 67–68, John Wiley & sons, N.Y.,N.Y., Aug. 13, 1981.*

Knight, G.D. et al. Seemingly Diverse Activities of B–Alethine. Cancer Research. Nov. 1, 1994, vol. 54, pp. 5636–5642, see especially Abstract, Figure 1 and p. 5636–5637.

* cited by examiner

Primary Examiner—Rebecca Cook
(74) Attorney, Agent, or Firm—Foley & Lardner

(57) ABSTRACT

The present invention relates to peptide-like compounds, e.g. aminocarboxylic acid amide derivatives, and to methods of using same to stimulate cells of the immune system, bone marrow and other organs. The present compounds can be used to enhance vaccination, increase synthesis of and enhance function of blood cell components and enhance anti-neoplastic effects of various agents. The compounds of the invention can be used to produce a variety of further pharmacologic effects.

2 Claims, No Drawings

LOW MOLECULAR WEIGHT COMPOUNDS ADMINISTERED TOGETHER WITH ANTI-CANCER AGENTS TO PREVENT OR TREAT CANCER AND PHARMACEUTICAL COMPOSITIONS THEREOF

This application claims priority to U.S. Provisional Application Nos.: 60/075,966 filed Feb. 24, 1998 and 60/085,474, filed May 14, 1998 which are incorporated herein in their entirety.

TECHNICAL FIELD

The present invention relates to peptide-like compounds, e.g. aminocarboxylic acid amide derivatives, and to methods of using same to stimulate cells of the immune system, bone marrow and other organs. The present compounds can be used to enhance vaccination, increase synthesis of and enhance function of blood cell components and enhance anti-neoplastic effects of various agents. The compounds of the invention can be used to produce a variety of further pharmacologic effects.

BACKGROUND

A variety of polypeptide cytokines, hormones and immune system modulators have been used to stimulate production and activity of bone marrow-derived cells. However, little progress has been made in obtaining the same physiologic activities in culture and in vivo using simple, chemically synthesized small molecules. For example, there are relatively few reports of the use of simple, small molecules in stimulating production and function of various blood components, including, without limitation, red blood cells (RBCs) and white blood cells (WBCs), in stimulating the response to vaccinations, in enhancing differentiation and in the nontoxic treatment of neoplasia. The present invention relates to such methods, as well as others, and to compounds suitable for use in same.

OBJECTS AND SUMMARY OF THE INVENTION

It is an object of the present invention to provide compounds that exert an immunomodulatory effect. It is another object of the invention to provide a method of altering (e.g. stimulating) cellular productivity and vitality and to provide a method of modulating cell growth.

It is a specific object of the invention to provide a method and compositions for modulating immune function, for example, to facilitate vaccination against or treatment of diseases, including infectious and autoimmune diseases, as well as other diseases in which the immune system plays a role.

It is another specific object of the invention to provide a method of effecting blood cell stimulation (including RBCs, WBCs, stem cells, platelets and others).

It is a further specific object of the invention to provide a method of enhancing cell differentiation and cell growth and a method of exerting an anti-senescence effect in vitro and in vivo. It is also a specific object of the invention to provide a method of preserving viability of neurons, natural killer (NK) cells, fibroblasts and other cell types in vivo and in vitro. It is a further specific object of the invention to provide a method of exerting anti-Alzheimer and anti-aging effects and a method of treating genetic diseases related to aging. It is a further object of the invention to provide a method of enhancing bioactivity of cosmetics and compounds to serve as cosmeceuticals.

It is also a specific object of the invention to provide a method and compositions for treating a neoplastic or pre-neoplastic condition. It is another object of the invention to provide a method of an ameliorating side effects of various anti-neoplastic agents.

It is a further specific object of the invention to provide a method of altering (e.g. stimulating) cellular protein production, including antibody production.

The foregoing objects are met by the present invention which provides aminocarboxylic acid amide derivatives that can be used to produce a variety of biomodulatory effects, both in vivo and in vitro.

Further objects and advantages of the present invention will be clear from the description that follows.

DETAILED DESCRIPTION OF THE INVENTION

In a first embodiment, the present invention relates to compounds of the formula (I):

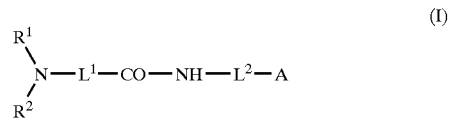

wherein:

A is a group of the formula —$PO_3H$, —$SO_3H$, —OPO—$(OH)_2$, —$OSO_2OH$, or —SH, or pharmaceutically acceptable salt thereof or physiolocally-hydrolyzable derivative thereof, or disulfide thereof when A is —SH. Suitable salts include sodium, potassium, calcium and zinc. Suitable hydrolyzable derivatizing groups include esters, such as substituted or unsubstituted lower alkyl (e.g. $C_1$ to $C_4$) or arylalkyl (e.g. benzyl) esters;

$R^1$ is H, a linear or branched lower alkyl, for example, a $C_1$ to $C_6$ alkyl, arylalkyl, for example, wherein the alkyl moiety is $C_1$ to $C_4$ alkyl and the aryl moiety is a substituted (e.g. lower alkyl or halogen) or unsubstituted phenyl group, or alkenyl (for example, $C_2$–$C_6$ alkenyl);

$R^2$ is H, a linear or branched lower alkyl, for example, a $C_1$ to $C_6$ alkyl, an alkenyl, for example, a $C_2$–$C_6$ alkenyl, an arylalkyl, for example, wherein the alkyl moiety is a $C_1$ to $C_4$ alkyl and the aryl moiety is a substituted (e.g. lower alkyl or halogen) or unsubstituted phenyl group; or an acyl, for example, acetyl, benzoyl, arylsulfonyl (for example, when the aryl moiety is phenyl); a carbonate ester such as alkoxycarbonyl (e.g., $C_1$–$C_7$ alkoxy carbonyl) (for example, —OCOC$(CH_3)_3$); allyloxy carbonyl (e.g. —OCOCH$_2$CH=CH$_2$); cycloalkoxycarbonyl (e.g. when the ring is $C_3$–$C_8$ ($C_5$–$C_6$ being preferred) and when the alkoxy moiety is $C_1$–$C_8$) (for example —OCOCH$_2$C$_5$H$_9$); or an unsubstituted arylalkoxycarbonyl (for example —OCOCH$_2$C$_6$H$_5$) or a substituted arylalkoxycarbonyl wherein the substituent is, for example, a halogen, a nitro group, an amino group or a methoxyl group;

alternatively, $R^1$ and $R^2$ taken together form, with the nitrogen to which they are attached, a 5 to 7 membered ring (for example, $R^1$ and $R^2$ taken together can be —(CH$_2$)$_4$—, —(CH$_2$)$_5$ or —(CH$_2$)$_6$—); and $L^1$ and $L^2$ are hydrocarbon linking groups, for example, a linear or branched chain alkyl of the formula —(C$_n$H$_{2n}$)— wherein n is, for example, 1 to 8 in the case of L$^1$ and 2 to 8 in the case of L$^2$ except when A is —PO$_3$H or —SO$_3$H in which case n can be 1–8; a cycloalkyl of 3 to 8 carbon atoms, preferably 5 or 6 carbon atoms; or an interphenylene

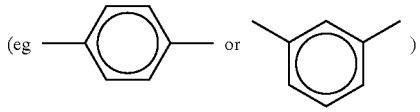

(eg — ⟨phenylene⟩ — or ⟨methylphenylene⟩ )

Advantageously, L$^1$ and L$^2$ are —(C$_n$H$_{2n}$)— wherein n is 1 to 8 in the case of L$^1$ or 2 to 8 in the case of L$^2$ except when A is —PO$_3$H or —SO$_3$H in which case n can be 1–8 (examples of branched chain alkyls include —CH$_2$CHR—, —CH$_2$CHRCH$_2$—, —CHRCH$_2$CH$_2$—, and —CH$_2$CH$_2$CHR— wherein R is an alkyl group and wherein the total number of carbon atoms, including R, does not exceed 8).

A particular group of compounds of the invention is of the formula (I) wherein A, R$^1$, R$^2$, L$^1$ and L$^2$ are as defined above in said first embodiment with the proviso that when A is —SO$_3$H or pharmaceutically acceptable salt thereof or physiologically hydrolyzable derivative thereof, one of R$^1$ and R$^2$ is H, and L$^1$ and L$^2$ are (CH$_2$)$_2$, then the other of R$^1$ and R$^2$ is not H.

Another particular group of compounds of the invention is of the formula (I) wherein A, R$^1$, R$^2$, L$^1$ and L$^2$, are as defined above in the first embodiment with the proviso that when A is —SO$_3$H or pharmaceutically acceptable salt thereof or physiologically hydrolyzable derivative thereof, one of R$^1$ and R$^2$ is H, and L$^1$ and L$^2$ are (CH$_2$)$_2$, then the other of R$^1$ and R$^2$ is not C$_6$H$_5$CH$_2$OCO—.

A further particular group of compounds of the invention is of the formula (I) wherein A is a group of the formula —PO$_3$H or —OPO(OH)$_2$, more particularly —PO$_3$H, or a pharmaceutically acceptable salt thereof or a physiologically hydrolyzable derivative thereof, and wherein R$^1$, R$^2$, L$^1$, and L$^2$ are as defined above in the first embodiment.

Another particular group of compounds of the invention is of the formula (I) wherein A is a group of the formula —SO$_3$H or —OSO$_2$OH, more particularly —OSO$_2$OH, or pharmaceutically acceptable salt thereof, or physiologically hydrolyzable derivative thereof, and wherein R$^1$, R$^2$, L$^1$ and L$^2$ are as defined above in the first embodiment. The provisos above can apply to this group of compounds as well.

A further particular group of compounds of the invention is of the formula (I) wherein at least one of R$^1$ and R$^2$ is an alkyl, advantageously a lower alkyl (e.g. C, to C$_6$), and wherein A, L$^1$, L$^2$ and the other of R$^1$ and R$^2$ are as defined above in the first embodiment.

Another particular group of compounds of the invention is of the formula (I) wherein R$^1$ is an alkyl and R$^2$ is acyl and wherein A, L$^1$ and L$^2$ are as defined above in the first embodiment.

A further particular group of compounds of the invention is of the formula (I) wherein L$^1$ is —(CH$_2$)— and wherein A, R$^1$, R$^2$, and L$^2$ are as defined above in the first embodiment.

Yet another particular group of compounds of the invention is of the formula (I) wherein R$^1$ and R$^2$ are taken together and form, with the nitrogen to which they are attached, a 5 to 7 membered ring, and wherein A, L$^1$ and L$^2$ are as defined above in the first embodiment.

The present compounds can also be present covalently bound to proteins, for example, antigens or other immunologically active proteins, or cell targeting proteins. Such conjugates can be synthesized using techniques known in the art.

The compounds of the present invention can be prepared using, for instance, methods provided in the Examples and in U.S. Pat. Nos. 4,102,948 and 4,218,404, as appropriate.

In another embodiment, the present invention relates to methods of using the above-described compounds in vivo and in vitro to alter (e.g. increase) cellular productivity and vitality and to modulate cellular differentiation, growth and/or function.

In vivo, the compounds can be used to elicit a variety of responses, including simulating bone marrow and platelet production, stimulating erythropoiesis, altering (e.g. increasing) immunogenic responsiveness and treating neoplasia. For example, the present compounds can be used to treat anemia and neutropenia. The compounds of the invention can be used to treat or prevent premature aging and degenerative diseases and to treat inherited metabolic diseases. The compounds of the invention can be used in the treatment of diseases of immune dysfunction including, without limitation, autoimmune diseases such as rheumatoid arthritis, diabetes, thyroiditis, lupus (SLE), connective tissue diseases, multiple sclerosis, sarcoidosis, psoriasis, hepatitis, and kidney diseases. The compounds can be used, for example, in the treatment of genetic diseases of aging (Ataxia telangiectasia, progeria and Werner's syndrome), in accelerated aging (as compared to the ultimate biologic potential of the organism), and in the treatment of Alzheimer's disease. The present compounds can be used to delay sensecence of fibroblasts, neural, lymphoid, epithelial, endothelial, mesenchymal, neuroectoderm, mesothelial and other cells, and to maintain function and health of aged cells and organisms.

The compounds can be used to cause an alteration in the number of cells of a particular cell type (e.g. epithelial cells or mesenchymal cells) (the compounds can be used, for example, to increase the number of red cells or white cells or the numbers of neuronal cells) or to cause an alteration in cellular function (e.g. an increase phagocytic activity of macrophage).

From the standpoint of immunogenic responsiveness, the present compounds can be used to enhance antigen processing, cell to cell communication, cellular immunity, natural immunity, humoral immunity, macrophage function, NK cell function, immune surveillance, immune response and immune killing. Further, the compounds of the invention can be used in conjunction with vaccination protocols to alter (e.g. increase) the response elicited by an antigen or an immunogenic conjugate. The present compounds can be used in vaccinations against infectious, neoplastic, autoimmune and other diseases. Specifically, the present invention can be used to enhance vaccinations to bacterial and viral diseases, for example, pneumonia, meningitis, TB, hepatitis B and HIV and to parasitic diseases. Further examples include bacterial diseases: *Pyogenic cocci* (staphylococci, pharyngitis, tonsillitis, sinusitis, streptococci, pneumococci, meningococci, gonococci), enteric bacilli (*Escherichia coli, Klebsiella, Salmonella shigella*), cholera, pseudomonas (*Pseudomonas aeruginosa, Pseudomonas mallei*), bacteroides, mycobacteria (tuberculosis), spirochetes (*Treponema pallidum* (syphilis)), clostridia, *Diphtheria hemophilus* and *Bordetella bacilli, Granuloma inguinale*, brucella, tularemia, anthrax, plague, mycoplasma, listeriosis; rickettsial disorders: typhus group, Rocky Mountain spotted fever, Lyme disease, scrub typhus, Q fever; chlamydial disorders: trachoma and inclusion conjunctivitis, lymphogranuloma venereum, and psittacosis; viral diseases: cutaneous viral infections (chickenpox, herpes zoster, measles), respiratory viral infections, viral diseases of the central nervous system, viral diseases of the liver, viral diseases of the salivary glands, and infectious mononucleosis; fungal diseases: candida albicans, mucor, histoplasmosis, aspergillosis, blastomycosis, coccidioidomycosis, actinomycosis and nocardiosis; and protozoal (parasitic) diseases: pneumocystosis, amebiasis, malaria, toxoplasmosis, leishmaniasis, trypanosomiasis, and giardiasis; helminths diseases (worms): trichinosis, strongyloidiasis, enterobius vermicularis, filariasis, hookworm disease, ascariasis, flukes, cestodes, tapeworms, and trichuriasis; and other diseases: sarcoidosis, cat-scratch disease, legionnaires' disease.

The compounds of the invention can also be used to inhibit the toxicity associated with immunotoxic and carcinogenic agents.

Depending on the effect sought and the clinical situation, the compounds of the invention can be administered before, during or after vaccination. Use of the present compounds can result in more effective injections and/or a reduction in the number of injections necessary for vaccination. The present compounds can also be used to treat infections, including chronic infections.

In a specific embodiment, the invention relates to a method of effecting isotype conversion using the compounds of the present invention. As shown in Example IX, the present compounds can be used to effect rapid induction of immunoglobulin G. These data demonstrate that the present compounds can be used to elicit a rapid response to a vaccine thereby reducing the number of injections necessary and/or increasing the efficiency of the each injection. The compounds of the invention can also focus antibody production of the polysaccharide and thus effect excellent responses to polysaccharide antigens, whether or not conjugated to a protein carrier.

As to neoplasia treatment, the compounds of the invention can be used to treat a variety of preneoplastic and neoplastic conditions, including both soft (e.g. hematolymphoid) and solid tumors (e.g. carcinomas and sarcomas). More specifically, the compounds of the invention can be used to treat breast cancer, prostate cancer, glioblastomas, melanomas, myelomas, lymphomas, leukemias, lung cancer, skin cancer, bladder cancer, kidney cancer, brain cancer, ovarian cancer, pancreatic cancer, uterine cancer, bone cancer, colorectal cancer, cervical cancer and neuroectodermal cancer, and premalignant conditions, including, without limitation, monoclonal gammapothies, dysplasia, including, without limitation, cervical and oral dysplasia. The compounds can also be used to treat conditions associated with altered differentiation (e.g. loss of pigmentation, hair; alteration of skin including psoriasis; alteration of gastrointestinal, kidney, liver, brain, endocrine, immune, lung, connective tissue, cardiac or other organ function).

The compounds of the invention can also be used to inhibit the toxicity associated with immunotoxic and carcinogenic agents. Conventional chemotherapeutic agents are highly toxic and have narrow therapeutic indices. Although conventional anticancer agents exhibit a certain degree of specificity for malignant cells, other rapidly proliferating cells, such as bone marrow cells, spermatogonia and cells of the gastrointestinal crypt epithelium, are very vulnerable to the toxic side effects of these agents. Cytotoxic agents can induce virtually every type of pathology on organ systems. Careful management of toxicity is therefore of paramount importance in managing patient care and there is a great need to diminish the toxicity of known anticancer agents. This is accomplished (i) by decreasing the effective dose of the toxic agent(s) to diminish the side effects without compromising effectiveness, or (ii) by decreasing toxicity where high doses of the agent(s) must be used, or if toxicity occurs over time even with relatively low doses.

It has now been discovered that compounds of Formula I including β-alethine, decrease the toxicity of known anticancer agents. Thus, the present invention is directed to new, less toxic anticancer pharmaceuticals which are mixtures that include one or more compounds of Formula I (β-alethine) and one or more known anticancer agents that can be either cell-cycle-specific or cell-cycle-nonspecific, and to methods of preventing or treating cancer by administering these compositions. It has also been discovered that combining compounds of Formula I combined with known anti-cancer agents produces a synergism in treating, preventing, and delaying the clinical appearance of primary cancer or metastatic cancer. One or more of the compounds of Formula I can be combined with one or more chemotherapeutic agents known to be effective in treating cancer, including but not limited to TAXOL™, cyclophosphamide, melphalan, levamisol NAC,5 fluorouracil, Methotrexate, Cisplatin, Carboplatin, Cyclophosphamide and Ifosfamide, Bleomycin, mAMSA, Streptozotocin, hydroxyurea, Etoposide, Doxycoformycin, Fludarabine, Chlorodeoxyadenosine, Doxorubicin and daunorubicin, Paclitaxel, Vincristein, Vinblastine, mAMSA, ThioTEPA, Epirubicin, 5-Fluorouracil, 6-Mercaptopurine, L-Phenylalanine mustard, MDR, MRP, Topoisomerase I, Topoisomerase II, Toxal, Vincristine, Vinblastine, Vindesine, VP-16, VM-26, Dactinomycin, Doxorubicin, Idarubicin, Mithramycin, Mitomycin-C, Bleomycin, Methotrexate, w/leucovorin, Methotrexate, 5-Fluorouracil, 5-Flourouracil w/leucovorin, 5-Fluorodeoxyuridine, 6-Mercaptopurine, 6-Thioguanine, Cytarabine, 5-Azacytidine, Hydroxyurea, Deoxycoformycin, Fludarabine, Cyclophosphamide, Ifosfamide and Mesna, Melphalan, CCNU, MeCCNU, BCNU, Chlorambucil, CBDCA (carboplatin), Aziridinylbenzoquinone (AZQ), DTIC (Dacarbazine), mAMSA, Procarbazine, Hexamethylmelamine, and Mitoxantrone.

This invention is also directed to methods of treating cancer or delaying the clinical appearance of cancer, by administering therapeutically effective amounts of the new β-alethine-containing anticancer mixtures. Cancer is typically treated by combination chemotherapy with the goal of controlling cancer cell proliferation and minimizing tumor burden. To ensure lysis of proliferating and resting cancer cells, combination chemotherapy is typically administered in cycles and drug combinations are chosen which have different mechanisms of action, produce synergy, and possess minimal overlapping toxicity. Chemotherapeutic agents are classified as either cell-cycle-specific agents which include plant alkaloids such as taxanes, or cell-cycle-nonspecific agents which include alkylating agents that alter DNA structure, such as cyclophosphamide and melphalan, antitumor antibiotics and hormones.

The most common dose-limiting side effect of chemotherapy is myelosuppression which, although generally reversible, in some cases causes death due to infection and bleeding complications. TAXOL™ is a well-known cell cycle-specific plant alkaloid agent used tp treat breast cancer. TAXOL™ is highly toxic and causes marked myelosuppression effects including neutropenia and thrombocytopenia, as well as cardiotoxicity. Serious toxic effects also result when the cell cycle-nonspecific agent cyclophosphamide is administered to treat melanoma or breast cancer, and when melphalan is administered to treat myeloma. These drugs are associated with causing moderate to marked myelosuppression, pulmonary toxicity, cardiotoxicity and neurotoxicity. Lippincott's Cancer Chemotherapy Handbook, D. C. Baquiran and J. Gallagher, 1–10, 59–107, 1998.

β-alethine (BT) has been reported to be an effective an anti-cancer agent when administered alone for treatment of all cancers, regardless of cell-lineage or phenotype. It has now been discovered that the addition of β-alethine and structurally or functionally similar compounds of Formula I to one or more other known anti-cancer agents decreases the toxicity observed when an equivalent doses of the anticancer agent(s) is administered alone. Further, β-alethine and structurally and functionally similar compounds of Formula I have a synergistic effect on preventing, treating or delaying the clinical appearance of cancer over administering either β-alethine or the anticancer agent alone. These results have been observed when Formula I compounds are combined anti-cancer agents drawn from both cell-cycle-specific and the cell-cycle-nonspecific categories. The embodiments of the present invention include the administration of compounds of Formula I to promote tumor regression, shorten the time to cure, increase the incidence of complete cures, decrease tumor volume and size prevent or reduce metastasis and protect against a second challenge with cancer.

In one embodiment, β-alethine is administered with the cell-cycle-nonspecific alkylating agent melphalan to treat cancer. In a series of experiments described in detail in Example XI, β-alethine was unexpectedly found to have a synergistic effect in treating the very aggressive MOPC-315 myeloma when combined with melphalan, compared to the administration of an equivalent dose of melphalan alone or β-alethine alone. Melphalan (mp) is the mainstay of human clinical therapy for multiple myeloma which is a chronic, progressive, and fatal disease in humans despite chemotherapy. Although the tumor burden in human patients with myeloma can be dramatically reduced by current chemotherapy and remissions of one to three years in duration are common, true cures are rare and typically associated with serious adverse side effects of mp.

It has been discovered that the combination of β-alethine/mp significantly increased overall survival, produced a five fold increase in the number of cures, prevented reoccurrence of the disease in cured animals even when challenged with a later injection of myeloma cells, promoted tumor regression and shortened the time to cure compared to the administration of an equivalent dose of mp or β-alethine alone. The present invention is also directed to a pharmaceutical composition including an mp in various relative amounts.

In another embodiment of the present invention, was administered together with another alkylating agent, cyclophosphamide (cp), to treat breast cancer in the MT-1 breast cancer xenograft model in mice. The combination of β-alethine/cp decreased the toxicity that was observed with β-alethine alone, and showed a synergistic effect on treating breast cancer over equivalent doses of cp or β-alethine administered alone. See Example XIII.

Mice having advanced MT-1 breast cancer tumors were given cyclophosphamide at doses of 300, 200 or 100 mg/kg, with our without administration of β-alethine 30 minutes earlier at 30 mg/kg. The addition of β-alethine to the very toxic dose of 300 mg/kg cp completely eliminated toxic deaths which occurred at the unacceptably high rate of 25% in the group receiving cp only. Further, the combination of β-alethine and cp caused most individual tumors to decrease in size, while most tumors grew in size in the group receiving cp alone. Therefore, in a preferred embodiment of the present invention, β-alethine is administered together with one or more known anti-cancer agents to reduce toxicity and or to treat or prevent cancer or to delay the clinical appearance of cancer. Another embodiment is a pharmaceutical composition including β-alethine and cp or any other known anti-cancer agent.

In another series of experiments, the combination of β-alethine/cp was used to treat the extremely fast-growing and aggressive solid melanoma B16. See Example XII. The combination was unexpectedly discovered to significantly decrease tumor size, and to result in fewer and smaller lung metastases while completely eliminating metastases to other organs, compared to treatment with an equivalent dose of either cyclophosphamide or β-alethine alone. Thus, in another embodiment of the present invention, a compound of Formula I is administered together with one or more known anti-cancer agents such as cyclophosphamide or melphalan to decrease metastatic cancer. Even in cases where surgery, radiation and chemotherapy are effective in eliminating the primary cancer, it is frequently the case that the patient dies from metastatic disease. The ability of the compounds of Formula I, especially β-alethine, to reduce metastases when administered together with one or more known anti-cancer agents, has immediate and important clinical applications in the treatment of aggressive melanoma and all cancers. A decrease in primary tumor volume was detected just five days after the onset of treatment with the β-alethine/cyclophosphamide mixture in animals with the extremely fats-growing and deadly B16 melanoma. In another preferred embodiment, β-alethine is administered together with cp to decrease, prevent or control metastasis.

In yet another embodiment, it was discovered that the combination of β-alethine significantly reduced the toxicity induced by paclitaxel (TAXOL™, or PAC) administered to non-tumor-bearing athymic mice (NCr-nu). See Example IV. Mice receiving the very toxic dose of 50 mg PAC together with 30 mg BT, suffered less weight loss at all time points, and showed a weight gain on day 21 that is twice the increase in weight gain observed with PAC alone. This indicates lower toxicity and an improvement in general wellness. PAC in an amount of 50 mg/kg is probably a fatal dose in humans.

Importantly, there were fewer toxic deaths when β-alethine was coadministered with either 30 mg or 50 mg paclitaxel. For the group receiving 50 mg PAC/30 mg β-alethine, the survival difference was statistically significant (log rank=6.41, p=0.0113). There were 9 deaths on day 21 with 50 mg PAC alone, and only 2 deaths with the β-alethine/PAC combination.

These results, taken together, demonstrate that compounds of Formula I, including β-alethine, combined with other anticancer agents unexpectedly lowered the toxicity of the anticancer agents with which it was combined. Further, the combination of compound of Formula I with one or more anti-cancer agents was much more effective in treating or preventing the onset cancer than an equivalent amount of the anticancer agent alone, regardless of the type of cancer or the anticancer agent.

The present invention relates to the combination of one or more anti-cancer agents with one or more compounds of Formula I to treat, prevent, or delay the clinical appearance of cancer to treat or prevent metastatic cancers, and/or to reduce the toxicity of other anti-cancer agents.

The amount of a compound of Formula I and other known anticancer agent to be administered to achieve the various embodiments of the present invention, can be determined by routine experimentation. For in vivo applications, the compounds of Formula I can be administered in amounts that vary from fg/kg to the maximum tolerated doses, together with a therapeutically useful, amount of any one or more known anticancer agent. In a preferred embodiment, compounds of Formula I are administered at Nanodrug™ doses of ng/kg to 2 g/kg and doses known in the art of anticancer agents. The compounds of Formula I decrease toxicity, which may permit moderate increases in the doses of the anti-cancer agents with which it is combined to obtain maximum effectiveness without increased risk of toxic death or adverse side effects. In preferred embodiments, the compositions of the present invention include one or more compounds or Formula I and cyclophosphamide, or melphalan, or Taxol™, or platinum containing drugs.

Although it may be generally advantageous to administer β-alethine in the mg/kg dose range along with known anticancer agents, the invention is not so limited. For example, use in ng/kg to fg/kg range may be optimal in certain circumstances such as maintenance chemotherapy or to prevent the clinical appearance of cancer, based on routine testing. Similarly, the amount of the anticancer agent combined with compounds of Formula I will vary with the individual, the type of cancer, and the extent of progress of the disease. For example, significantly lower doses of β-alethine and the anticancer agent may be sufficient for maintenance chemotherapy, for pediatric use, or for periodic administration after a certain period of remission to prevent the reappearance or metastasis of cancer.

The compounds of the invention can be administered topically, orally, rectally, intravaginally intravenously, intraperitoneally, subcutaneously, intramuscularly or intranasally, as appropriate for the effect sought. The compounds can also be administered transdermally using, for example, transdermal patches or transmucosally via sprays or other application.

The compounds of the invention are typically used in the form of a pharmaceutical composition comprising the compound of formula I, or salt or hydrolyzable derivative thereof as described above, together with a pharmaceutically acceptable diluent or carrier. The composition can be present in dosage unit form, for example, as a tablet, capsule or suppository. The composition can be formulated so as to be suitable for topical application (e.g. as a gel, cream, lotion or ointment). Alternatively, the composition can be present as a solution or suspension (e.g. sterile) suitable for administration by injection, inhalation, intranasally or dropwise to the eye or other sites as appropriate. The compound of the invention can be prepared as a slow release formulation appropriate for internal or external use. Using techniques known in the art, the compounds of the invention can also be trapped in or bound to a polymer, a solid support, a liposome or a gel.

Carriers and diluents known in the art can be used and the composition, when, for example, in the form of a tablet or capsule, can be formed with an enteric coating.

The composition of the invention can include active agents in addition to the compounds of formula I. Examples of such additional active agents include cancer chemotherapeutic agents, hormones, vitamins, cytokines, enzyme regulators, regulatory macromolecules, regulatory thiols or other small molecules.

The present compounds also have ex vivo applications including in the growth, maintenance or differentiation of tissue grafts, including bone and vascular grafts, and in the treatment of cells and organs, for example, prior to transplantation or use in the laboratory.

While the compounds of the invention are suitable for therapeutic use in humans, the compounds of formula I are also useful in the veterinary treatment of similar conditions affecting warm-blooded animals, such as dogs, cats, horses, cattle or birds, or fish. For such purposes, the compounds of the formula I can be administered in an analogous amount and manner to those described above for administration to humans. The compounds of the invention also have application to lower organisms, including insects, reptiles, and plankton, microorganisms, or others. They can be used in aqueous environments, including in marine or fresh water settings.

The present compounds are useful in connection with intact animals (particularly, but not exclusively, mammals) cells, tissues and organs.

Cells can be grown or stored in the presence of the present compounds using any of a variety of available techniques, including growth on plastic or glass or other support (e.g. beads or hollow fibers), growth in suspension (e.g. in liquid or semisolid medium), growth in a bioreactor, or storage in a frozen or dried state. Primary cultures or serial cultures, or otherwise, can be used.

The amount of the compound of the invention to be used and the frequency of exposure can be readily determined by one skilled in the art and will vary with the cell type, the compound used and the effect sought. In determining optimum concentrations, appropriate in vitro assays are run in the femtogram/ml to 10's of mg/ml range.

Various aspects of the present invention are described in greater detail in the non-limiting Examples that follow. Certain of the synthetic procedures described below correspond to those described by Knight et al, Cancer Research 54:5623 (1994) or in U.S. Pat. No. 4,218,404, or represent modifications thereof. In addition, the disclosures of WO 92/00955 and PCT/US91/04725 are relevant here, including the portions therein that relate to syntheses, therapeutic regimens and cell culture treatment protocols, those regimens and protocols being applicable to the compounds of the present invention.

EXAMPLE I

Synthesis of N-Carbobenzoxy-β-Alanyl-Taurine Zinc Salt

Method I

Preparation of N,N'-bis(CBZ)-β-Alethine from N-CBZ-β-alanine

To a 250 ml round bottom flask were added a stir bar, N-CBZ-alanine (5.805 g, 26.008 mmol), N-hydroxysuccinimide (2.993 g, 26.008 mmol, 1 eq.), and 1,3-dicyclohexylcarbodiimide (5.366 g, 26.008 mmol, 1 eq.). The flask was sealed with a septum and purged with argon. $CH_2Cl_2$ (86 ml) was then added and the mixture stirred overnight at room temperature (rt). All of the solids did not dissolve upon addition of $CH_2Cl_2$. The solids were then removed via vacuum filtration through a pre-argon-purged medium glass fritted buchner funnel. The funnel was equipped with an argon purge funnel and a 500 ml round bottom flask containing a stir bar and cystamine$2HCl (1.464 g, 6.502 mmol, 0.25 eq.). The flask and solids (white) were then rinsed with 3×15 ml $CH_2Cl_2$. The filtrate was colorless to light yellow. The flask was removed from the buchner, sealed with a septum and purged with argon. To the stirring solution was added $Et_3N$ (2.9 ml, 20.806 mmol, 0.8 eq.). All of the solids did not dissolve. The reaction was stirred overnight at room temperature. The product was then collected using an 11 cm buchner funnel with #541 Whatman filter paper. The flask and solids (white) were rinsed with 3×15 ml CH$_2$Cl$_2$. The filtrate was colorless to yellow. The solids were placed in a 250 ml round bottom flask and dried under high vacuum overnight. The crude product weight was determined and DMSO (0.3 g/ml) was added and heated to 70° C.–90° C. to dissolve the solids with the aid of stirring. H$_2$O (0.12 g/ml) was then added slowly with vigorous stirring. The mixture was cooled to room temperature and collected after 3 hours using an 11 cm buchner funnel with #541 Whatman filter paper. The solids (white) and flask were rinsed 3×15 ml CH$_2$Cl$_2$ H$_2$O followed by 2×15 ml EtOAc. The solids were chopped-up with a spatula and dried under high vacuum in a 250 ml round bottom flask. The recovery was 3.568 g corresponding to a 97.5% yield.

Preparation of N-carbobenzoxy-β-alanyl-taurine Zinc Salt from N,N'-bis(CBZ)-β-alethine (Small Additions of ZnO or Ca(OH)$_2$)

To a 250 ml erlenmeyer flask were added a stir bar, N,N'-bis(CBZ)β-alethine (2.524 g, 4.486 mmol), dimethylsulfoxide (2.5 ml), N,N-dimethylformamide (2.5 ml), pyridine (3.2 ml), CHCl$_3$ (75 ml), and H$_2$O (150 ml). The mixture was stirred vigorously giving an emulsion (not all solids dissolved). A pH meter was immersed in the aqueous phase. The pH was near 7.3 to 7.7. I$_2$ (7.97 g, 31.401 mmol, 7 eq.) was then added. Initially the organic phase was red and the aqueous phase was colorless. During the reaction, the color of the aqueous phase darkened to red and the emulsion subsided. The pH dropped to 5.7 within 10 minutes of adding I$_2$. ZnO (100–200 mg, 0.3–0.6 eq.) was added in portions to keep the pH between 5.7 and 6.0. After ~3.5 hours, the pH stabilized and the reaction was allowed to stir for an additional 2 hours (5.5 h total reaction time). The phases were separated (organic was dark red) and the aqueous phase was washed with 10 ml CHCl$_3$. The aqueous phase (light red) was extracted additionally with CHCl$_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolved in 1 ml H$_2$O and 3 ml acetonitrile and added to 100 ml acetonitrile. The white precipitate was collected on a #541 Whatman filter paper and rinsed with 40 ml acetonitrile. The recovery was 1.676 g of white solids corresponding to a 52% yield (N-carbobenzoxy-β-alanyl-taurine zinc salt).

Preparation of N-carbobenzoxy-β-alanyl-taurine Zinc Salt from N,N'-bis(CBZ)β-alethine (ZnO Added Initially)

To a 125 ml erlenmeyer flask were added a stir bar, N,N'-bis(CBZ)β-alethine (809 mg, 1.438 mmol), dimethylsulfoxide (0.8 ml), N,N-dimethylformamide (0.8 ml), pyridine (1.0 ml), CHCl$_3$ (24 ml), H$_2$O (80 ml), and ZnO (526 mg, 6.470 mmol, 4.5 eq.). The mixture was stirred vigorously giving an emulsion (not all solids dissolved). I$_2$ (3.28 g, 12.904 mmol, 9 eq.) was then added. Initially, the organic phase was red and the aqueous phase was colorless. During this reaction, the color of the aqueous phase darkened to red and the emulsion subsided. The mixture was stirred overnight. The phases were then separated (organic was dark red) and the aqueous washed with 20 ml CHCl$_3$. The aqueous phase (light red) was extracted additionally with CHCl$_3$ using a continuous liquid/liquid extractor overnight. The aqueous phase (colorless to very light pink) was separated, partially evaporated on a rotary evaporator to remove dissolved organics, shelf frozen, and lyophilized. The residue (golden brown) was dissolved in 0.5 ml H$_2$O and 2 ml acetonitrile and added to 75 ml acetonitrile. The white precipitate was collected on a #541 Whatman filter paper and rinsed with 20 ml acetonitrile. The recovery was 630 mg of white solids corresponding to a 61% yield (N-carbobenzoxy-β-alanyl-taurine zinc salt).

The $^{13}$C NMR spectral data were as follows:

| Signal | DMSO solvent:C—H coupled |
|---|---|
| 1 | 48.4 |
| 2 | 33.8 |
| 3 | 172.2 |
| 4 | 34.6 |
| 5 | 36.4 |
| 6 | 156.4 |
| 7 | 65.4 |
| 8 | 135.0 |
| 9 | 125.8 |
| 10 | 126.5 |
| 11 | 128.0 |

Method IIa

Preparation of N-carbobenzoxy-β-alanyl-taurine (Free Acid and Zinc Salt) from N-(CBZ)-β-alanine The N-(CBZ)-β-alanine (563 mg, 2.522 mmol), N-hydroxysuccinimide (290 mg, 2.522 mmol) and DCC (520 mg, 2.522 mmol) were dissolved (no obvious dissolution) in CH$_2$Cl$_2$ (11.5 ml, to make a 0.22 M solution). The reaction was allowed to mix overnight at room temperature. The crude reaction mixture was filtered through a sintered glass funnel to remove the dicyclohexylurea (DCU). The reaction was filtered "anhydrously" into a flask containing 316 mg (2.522 mmol) taurine. The filter cake was washed with 3, 5 ml volumes of CH$_2$Cl$_2$. After adding 316 μl Et$_3$N (1 eq), the reaction was allowed to mix at room temperature. The reaction was allowed to mix until complete by NMR. The crude reaction mixture was purified by trituration with MeCN. The crude reaction mixture was dissolved in 14 ml CH$_2$Cl$_2$ (0.2 M) and 1 eq of triflic acid was added. The reaction was allowed to mix overnight at room temperature although the reaction appeared complete after mixing for only 15–20 minutes. The reaction mixture was filtered and the filter cake washed with CH$_2$Cl$_2$. The filter cake (the free acid) was divided into two portions. One portion (305 mg) and 0.5 eq Zn(OH)$_2$ were dissolved in 5 ml H$_2$O and allowed to mix for 1 hour and then it was concentrated by lyophilization to give 340 mg as a white solid (66% based on starting N-(CBZ)-β-alanine). The other portion was purified and characterized as the free acid (190 mg). NMR data were obtained on both the free acid and the Zn salt, the Zn salt being the more pure.

The $^1$H NMR spectral data were as follows:

| Signal | D$_2$O solvent |
|---|---|
| a | 2.99(t, J=12.8Hz, 2H) |
| b | 3.48(t, J=12.8Hz, 2H) |
| c | not seen due to hydrogen bonding |
| d | 2.38(t, J=12.4Hz, 2H) |
| e | 3.35(m, 2H) |
| f | not seen due to hydrogen bonding |
| g | 5.07(m, 4H) |

The $^{13}$C NMR spectral data were as follows:

| Signal | DMSO solvent |
|---|---|
| 1 | 51.1 |
| 2 | 36.1 |
| 3 | 170.2 |
| 4 | 36.4 |
| 5 | 37.7 |
| 6 | 156.6 |
| 7 | 65.7 |
| 8 | 137.8 |
| 9 | 128.3 |
| 10 | 128.9 |
| 11 | 128.9 |

Method IIb

Preparation of N-carbobenzoxy-β-alanyl-taurine (Free Acid and Zinc Salt) from N-(CBZ)-β-Alanine (Scale Up)

In a three-neck 1L flask was placed CBZ-β-alethine (48.2 g, 215.9 mmol) under $N_2$. To this was added freshly distilled methylene chloride (750 mL), followed by N-hydroxysuccinimide (24.85 g, 215.9 mmol). To the resulting suspension was added 1,3-dicyclohexylcarbodiimide (DCC, 44.54 g, 215.9 mmol). At this scale the reaction generated a noticeable exotherm, sufficient to reflux the $CH_2Cl_2$. The reaction mixture was stirred under $N_2$ for 5 hours at which point the mixture was filtered through a sintered glass buchner funnel. The filter cake was washed with $CH_2Cl_2$ (3×100 mL). To the filtrate was added taurine (27.03 g, 215.9 mmol) and triethylamine (33.1 mL, 237.5 mmol). The reaction was stirred under $N_2$ and monitored by $^1$H-NMR analysis. The reaction mixture was vacuum filtered through a buchner funnel using Whatman #542 filter paper. The filtrate was stripped to an oil using reduced pressure, then placed on high vacuum. The "oil" was triturated with acetonitrile with one drop of water to quench any unreacted DCC. The mixture was filtered and the MeCN was stripped off under reduced pressure then placed on high vacuum. The resulting oil was dissolved in water (50 mL). A curdy white precipitate formed, more water (150 mL) was added and the resulting solid was filtered off. In the filtrate an oil precipitated out of solution. $^1$H-NMR spectra were obtained to determine the location of product. The product was in the aqueous layer as expected. The aqueous phase containing the product was then eluted through a H+ ion exchange column. Fractions (225 mL) were collected and spotted on TLC. The desired product was found in fractions 2–7. These fractions were combined and the water removed under reduced pressure. To the resulting oil was added MeCN (1L) and the solution was stirred. The remaining water was removed by azeotropic distillation with the MeCN. The resulting solid was collected by vacuum filtration and washed with MeCN. The solid was vacuum dried in a 1L round bottom flask then transferred to a tared 4 oz. amber bottle. Final package weight was 38.89 g (117.7 mmol, 54.5% yield). The zinc salt was prepared by treatment with $Zn(OH)_2$ in $H_2O$, followed by lyophilization. The spectral data for the product matched exactly a standard sample of N-carbobenzoxy-β-alanyl-taurine zinc salt.

EXAMPLE II

Synthesis of β-Alanyl-Taurine (Free Acid and Zinc Salt)

N-carbobenzoxy-β-alanyl-taurine (1.00 g, 3.4 mmol) was slurried in 23 ml glacial AcOH. To the mixture was added 3.4 mL HBr in AcOH (30 wt %) to result in a clear solution. The reaction was heated to 40° C. and allowed to mix overnight. The product precipitated out of solution and acetonitrile was added to force the precipitation. The mixture was filtered, the filter cake washed and the product collected. The crude Br salt was loaded onto an ion exchange column (Dowex AG1-XB8). The column was eluted with $H_2O$. The product cut was collected and lyophilized to give 583 mg of β-alanyl-taurine (87.3%). The zinc salt was prepared by treatment with $Zn(OH)_2$ in $H_2O$, followed by lyophilization.

The $^1$H NMR spectral data were as follows:

| Signal | $D_2O$ solvent |
|---|---|
| a | 3.09(t, J=12Hz, 2H) |
| b | 3.59(t, J=12Hz, 2H) |
| c | not seen due to hydrogen bonding |
| d | 2.66(t, J=12Hz, 2H) |
| e | 3.25(t, J=12Hz, 2H) |

The $^{13}$C NMR spectral data were as follows:

| Signal | DMSO solvent |
|---|---|
| 1 | 50.8 |
| 2 | 36.2 |
| 3 | 169.6 |
| 4 | 33.1 |
| 5 | 36.2 |

For comparison, β-alanyl-taurine zinc salt prepared using the method of Knight et al, Cancer Research 54:5623 (1994) gave the following $^1$H NMR spectra:

| Signal | $D_2O$ solvent |
|---|---|
| a | 2.93(t, J=12Hz, 2H) |
| b | 3.42(t, J=12Hz, 2H) |
| c | not seen due to hydrogen bonding |
| d | 2.50(t, J=12Hz, 2H) |
| e | 3.10(t, J=12Hz, 2H) |

EXAMPLE III

Preparation of N-Carbobenzoxy-β-Alanyl-Ethanolamine Phosphate (Free Acid and Zinc Salt) from N-(CBZ)-β-Alanine N-(CBZ)-β-alanine (274 mg, 1.23 mmol), N-hydroxysuccinimide (141 mg, 1.23 mmol) and dicyclohexylurea (DCC, 253 mg, 1.23 mmol) were dissolved in tetrahydrofuran (THF, 4.1 mL). The reaction was allowed to mix at room temperatore overnight before being filtered to remove the dicyclohexylurea (DCU). To the filtrate, a solution of 2-aminoethyl dihydrogen phosphate (1.23 mmol) in $H_2O$ (0.5 ml) was added. To the reaction mixture was added 2.1 molar equivalents of triethylamine. The reaction was allowed to mix for three days before the THR was removed under vacuum. The remaining aqueous phase was filtered and loaded onto a prepared ion exchange column (Dowex AG 50W-X8). The column was eluted with water. The product fractions were collected and lyophilized. The crude solid (260 mg) was treated with 1.0 molar equivalents of Zn(OH)$_2$ in H$_2$O to make the salt. The crude solid (after lyophilization) was triturated with acetronile and collected (50 mg).

EXAMPLE IV

Synthesis of N-Carbobenzoxy-β-Alanyl-Aminoethylphosphonic Acid (Free Acid and Zinc Salt) from N-(CBZ)-β-Alanine N-(CBZ)-β-alanine (301 mg, 1.35 mmol), N-hydroxysuccinimide (155 mg, 1.35 mmol) and dicyclohexylurea (DCC, 278 mg, 1.35 mmol) were dissolved in tetrahydrofuran (THF, 4.5 ml). The reaction was allowed to mix at room temperature overnight before being filtered to remove the dicyclohexylurea (DCU). To the filtrate, a solution of 2-aminoethylphosphonic acid (1.35 mmol) in H$_2$O (0.5 ml) was added. To the reaction mixture was added 2.1 molar equivalents of triethylamine. The reaction was allowed to mix for three days before the THF was removed under vacuum. The remaining aqueous phase was filtered and loaded onto a prepared ion exchange column (Dowex AG 50W-X8). The column was eluted with water. The product fractions were collected and lyophilized. The crude solid (270 mg) was treated with 1.0 molar equivalents of Zn(OH)$_2$ in H$_2$O to make the salt. The crude solid (after lyophilization) was triturated with acetonitrile and collected (50 mg).

EXAMPLE V

In Vitro Simulation of Differentiation and Production of Differentiated Product by N-Carbobenzoxy-β-Alanyl-Taurine Zinc Salt Hybridoma cells (ATCC #CRL-8014, OKT-8, secreting an IgG2 anti-human T-cell subset antibody) were growth with or without N-carbobenzoxy-β-alanyl-taurine zinc salt in T25 culture flasks. Cells were inoculated at a density of 10,000 cells/ml and maintained below 500,000 cells/ml in 5 mls of protein-free media containing HyQ-PF-MAB from Hyclone. Aliquots were assayed for Mab production by a sandwich ELISA. Aliquots were diluted to be within the standard range and added to plates precoated with goat anti-mouse IgG by incubating two hours at room temperature. Wells were washed and reacted with diluted supernatants, then washed and detected with peroxidase labeled anti-mouse antibodies. The results are shown in Table 1.

TABLE 1

Altered Production of Monoclonal Antibodies from Hybridomas

| Drug | IgG, μg/ml | IgG, pg/cell |
| --- | --- | --- |
| 0 - control | 12 | 41.7 |
| N-carbobenzoxy-β-alanyl-taurine 200 pg/ml | 50 | 80.6 |
| Increase | 316% | 93% |

EXAMPLE VI

Stimulation of Protein Production from Mammalian Cells

CHO cells containing a cloned gene for tissue plasminogen activator (tPA) were obtained from ATCC as #CRL-9606. The tPA gene had been introduced by transfection of a plasmid pETPFR. The cells were propogated in T-25 flasks in Ham's F-12 medium with 10% fetal bovine serum. The cell cultures were innoculated by adding 5 ml of cells at 2×10$^4$ cells/ml into T-25 flasks.

The effect of N-carbobenzoxy-β-alanyl taurine zinc salt on the production of tPA was tested by adding this compound to the growth medium, and maintaining the indicated levels of the compound over many (e.g. 6) passages of the cells.

At the end of log phase growth, the cultures were harvested by trypsinization. One ml was centrifuged to remove cells and the supernatant assayed for tPA in the IMUBIND total tPA Stripwell ELISA from American Diagnostica Inc.

The results shown in Table 2 demonstrate that the compound (N-carbobenzoxy-β-alanyl taurine zinc salt, #'s 1, 2 and 3 in Table 2) alters the per-cell production of tPA by about 2 fold. The cell numbers per milliliter were determined by direct counting of trypan-blue stained cells on a hemacytometer.

TABLE 2

| Compound | ELISA Optical Density | Supernatant Concentration nanograms/ml* | Culture Cell Density | Picograms tPA per cell |
| --- | --- | --- | --- | --- |
| Control | 0.177 | 424.6 | 2.2 × 10$^5$ | 1.93 |
| #1 | 0.332 | 1,492.8 | 4.0 × 10$^5$ | 3.73 |
| 1 pg/ml | | [3.5 × control] | | [1.9 × control] |
| #2 | 0.317 | 1,389.4 | 4.8 × 10$^5$ | 2.89 |
| 1 pg/ml | | [3.3 × control] | | [1.5 × control] |
| #3 | 0.422 | 2,113.0 | 5.2 × 10$^5$ | 4.06 |
| 1 pg/ml | | [5.0 × control] | | [2.1 × control] |

*The standard curve is "Abs = 0.1154 + .029* Concentration", with a correlation coefficient of 0.9977.

EXAMPLE VII

In Vivo Coordinated T Cell Dependent Response Delayed Type Hypersensitivity

In order to test an in vivo coordinated T cell dependent response, delayed type hypersensitivity (DTH) was measured. DTH is the test used clincially to determine if a person has mounted an immune response to many antigens. The most frequent application is measurement of DTH in response to tuberculosis called a PPD or tine test. It is also used to determine if a patient, such as a cancer patient, has had a failure of the immune system and become anergic.

In the laboratory this test involves the generation of a specific response to a oxazalone (OX) in mice and measurement of the response. The generation of the response (sensitization or initial exposure) was caused by the application of OX to the shaved abdomen of the animal (50 μl of 1.2% OX in olive oil). Measurement of the response occurred 24 and 48 hours following application of OX (5 μl 1.2%) to the right ear of the animal. In the experiment performed, sensitization occurred on day 0; challenge occurred on day 4. On days five and six, the thickness of the ear was measured and the thickness before challenge was subtracted. The doses of OX used were chosen so that some normal untreated animals had a perceptible but moderate response to the OX at 24 hrs.

In order to measure the effect of N-carbobenzoxy-β-alanyl-taurine zinc salt, various doses were injected iv on Day -2, 0, +2 and +4.

Ten animals were used per group. Drug dilutions are made up and coded at one facility and an independent contract facility (Midlantic Research) performed all procedures in a "blind" fashion. In no case did control ears (those either not sensitized or not challenged) have swelling over 40μ. Animals with 50μ to 99μ swelling were rated as having moderate swelling. Three control (saline injected) animals mounted a moderate response on at 24 hrs as expected. N-carbobenzoxy-β-alanyl taurine altered the response rate to eight of ten in two different treatment groups (this is above the 95% confidence bounds for an altered response by relative risk measure). All groups of animals receiving between 1 fg/kg and 1 mg/kg had more moderate responders than the saline injected group.

Those animals with 100μ or greater swelling were rated as having major immune responses. No saline injected animal had major immune response at 24 hours while a total of 14 N-carbobenzoxy-β-alanyl-taurine treated animals had major immune response. One non drug treated animal had a major response at either 24 or 48 hours post challenge, while 21 N-carbobenzoxy-β-alanyl-taurine treated animals had a major response at one of these times. The data are presented in Table 3.

| Dose/kg > | 0 | 1 fg | 32 fg | 1 pg | 32 pg | 1 ng | 1 μg | 1 mg |
|---|---|---|---|---|---|---|---|---|
| Moderate DTH at 24 hrs | 30 | 70 | 60 | 50 | 80* | 80* | 40 | 70 |
| Major DTH at 24 hrs | 0 | 20 | 20 | 10 | 10 | 20 | 10 | 50* |
| Major DTH at 48 hrs. | 0 | 20 | 20 | 10 | 10 | 20 | 10 | 50 |
| Major DTH at either 24 or 48 hrs. | 10 | 20 | 20 | 10 | 40 | 20 | 30 | 60 |

*Relative Risk (RR) compared to control exceeds 1 even at lowest end of 95% confidence bounds. RR not tested at 48 hours

EXAMPLE VIII

Blood Cell Stimulation

A 96-well-based suspension culture system (Warren et al, Stem Cells 13:167 (1995) for human hematopoietic progenitor cells was used to monitor the commitment and differentiation of CD34+ cells in vitro. Expression of maturation and lineage markers on the cells in culture were measured by ELISA. The CD34+ cells were isolated from umbilical cord blood (90% purity) and grown in liquid culture in 96-well plates (2000 per well) for 10 days. A combination of growth factors was added that stimulates the expression of the appropriate lineage markers. The culture consisted of: IMDM plus 15% FBS, 0.5 ng/ml IL-3, 20 ng/ml SCF, 1 unit/ml EPO, 1 ng/ml GCSF and the indicated concentrations of test compounds. The cells were then fixed with a glutaraldehyde-paraformaldehyde mixture, attaching the cells firmly to the plastic. An ELISA was performed (Warren et al, Stem Cells 13:167 (1995)), using appropriate primary antibodies directed against cell surface markers. The expression of three different lineage markers was measured: CD14 (monocyte), CD15 (neutrophil), and glycophorin A (erythroid). The results are presented in Table 4.

TABLE 4

Increase in Blood Cell Production
Percent difference (relative to control)

| | Study 1: 1 ng/ml compound | | | Study 2: 1 ug/ml | | |
|---|---|---|---|---|---|---|
| Compound | monocytes | neutrophils | red blood cells | CD34 cells | monocytes | RBC |
| Taurox-BP | 18 | 14 | 1 | 0 | 2 | 4 |
| Taurox-BOP | 18 | 21 | 0 | 33 | 9 | 55 |
| Taurox-SB | 15 | 0 | 0 | not tested | | |
| Taurox-S | 47 | 55 | 50 | not tested | | |

Taurox-BP = N-carboxybenzoxy-β-alanyl aminoethylphosphonic acid
Taurox-BOP = N-carboxybenzoxy-β-alanyl-ethanolamine phosphate
Taurox-SB = N-carboxybenzoxy-β-alanyl-taurine
Taurox-S = β-alanyl-taurine
Study 2: same, expect 1700 cells per well

EXAMPLE IX

Immune Stimulation

BALB/c female mice (4–5 weeks of age) were pre-bled, then injected ip with 0.1 mls of indicted compounds on day −7, day −5, day −3, and day 0. On day 0, they received soluble polysaccharide antigen Pn14-Tetanus Toxin, 10 μg in 0.1 mls, given ip. Two other groups received Pn14-TT, 10 μg in 0.1 mls of a 60% emulsion of complete Freund's adjuvant (CFA) on Day 0, given subcutaneously above the hind leg, just off the midline. The two CFA groups were treated identically. All mice were bled on Day 4 and Day 14. On Day 84, mice were bled and boosted with 5 μg Pn14 (not conjugated to TT) and either the experimental compound or incomplete Freund's adjuvant (for those previously given CFA). Mice were bled on day 94. Sera at 1:1000 were analyzed by ELISA for anti-Pn14 antibodies. Prebleed values were subtracted.

TABLE 5

Mean Change in O.D. (Optical density, indicating presence of antibody)

| | Change from pretest to 4 & 14 days after injection with antigen | | Change from pre-boost 10 days after boost with UNCONJUGATED |
|---|---|---|---|
| Compound (per kg) | Day 4 | Day 14 | polysaccharide |
| CFA (control) | −0.6 | 672 | −256 |
| CFA (control) | −1.0 | 367 | not tested |
| Taurox-BP, 5 ng | 15.5 | 1399 | not tested |
| Taurox-BP, 5 ug | 6.5 | 616 | not tested |
| Taurox-BP, 5 mg | 3.3 | 924 | 187 |
| Taurox-BOP, 5 ng | 5.4 | 877 | not tested |
| Taurox-BOP, 5 ug | 1.8 | 515 | not tested |
| Taurox-BOP, 5 mg | 0 | 366 | not tested |
| Taurox-SB, 5 ng | 6.2 | 705 | not tested |

TABLE 5-continued

Mean Change in O.D. (Optical density, indicating presence of antibody)

| Compound (per kg) | Change from pretest to 4 & 14 days after injection with antigen | | Change from pre-boost 10 days after boost with UNCONJUGATED polysaccharide |
|---|---|---|---|
| | Day 4 | Day 14 | |
| Taurox-SB, 5 ug | 3.9 | 483 | not tested |
| Taurox-SB, 5 mg | 1.1 | 697 | 139 |
| Taurox-S, 5 ng | 13.1 | 681 | 204 |
| Taurox-S, 5 ug | 3.6 | 671 | not tested |
| Taurox-S, 5 mg | 2.9 | 697 | not tested |

Notes
1. Values are the mean of 3 animals per drug/dose group.
2. Doses were 5 ng per kilogram of animal, 5 ug/kg, and 5 mg/kg of test compounds given prior to and with conjugated antigen, indicated above as "ng", "ug", and "mg".
3. CFA—Complete Freund's adjuvant, the current "gold standard" vaccine adjuvant, but approved only for animal uses due to its toxicity. Two groups of 3 animals were used. Published data indicate CFA stimulates response 10x compared to saline.

Discussion a. Only in animals treated with a compound of this invention is a 4-day response seen.
b. Only in animals treated with a compound of this invention is a response to unconjugated polysaccharide seen.
c. The 14-day response is greater with treatment.

EXAMPLE X

Syntheses

Synthesis of N-Carbobenzoxy-β-Alanyl-Ethanolamine Sulfate—Taurox BOS

To a THF solution of N-(CBZ)-β-alanine and N-hydroxysuccinimide, add DCC. The reaction is mixed overnight at room temperature. The crude reaction mixture is filtered through a sintered glass funnel into a round bottom flask to remove the DCU that is formed. The activated ester should remain in solution. After concentrating and redissolving in solvent, ethanolamine or an alcohol protected derivative can be added as a solution to the solution containing the activated ester. Triethylamine can also be added. Workup of the reaction and purification results in formation of N-carbobenzoxy-β-alanyl-ethanolamine. The free alcohol can be sulfated by a variety of methods to result in formation of N-carbobenzoxy-β-alanyl-ethanolamine sulfate.

Synthesis of β-Alanyl-Ethanolamine Sulfate (from N-Carbobenzoxy-β-Alanyl-Ethanolamine Sulfate)—Taurox OS In a similar fashion to the conversion of N-carbobenzoxy-β-alanyl-taurine to β-alanyl-taurine, N-carbobenzoxy-β-alanyl-ethanolamine sulfate can be converted to β-alanyl-ethanolamine sulfate. The conversion can be effected by slurrying the N-carbobenzoxy-β-alanyl-ethanolamine sulfate in glacial AcOH. To the mixture, HBr in AcOH (30 wt %) is added. The reaction can be heated and allowed to mix for a period of not less than 1 hour. The product can be isolated by usual workup and precipitation.

Synthesis of β-Alanyl-Ethanolamine Phosphate (from N-Carbobenzoxy-β-Alanyl-Ethanolamine Phosphate)—Taurox OP In a similar fashion to the conversion of N-carbobenzoxy-β-alanyl-taurine to β-alanyl-taurine, N-carbobenzoxy-β-alanyl-ethanolamine phosphate can be converted to β-alanyl-ethanolamine phosphate. The conversion can be effected by slurrying the N-carbobenzoxy-β-alanyl-ethanolamine phosphate in glacial AcOH. To the mixture, HBr in AcOH (30 wt %) is added. The reaction can be heated and allowed to mix for a period of not less than 1 hour. The product can be isolated by usual workup and precipitation.

Synthesis of β-Alanyl-Aminoethylphosphonic Acid (from N-Carbobenzoxy-β-Alanyl-Aminoethylphosphonic Acid)—Taurox P In a similar fashion to the conversion of N-carbobenzoxy-β-alanyl-taurine to β-alanyl-taurine, N-carbobenzoxy-β-alanyl-aminoethylphosphonic acid can be converted to β-alanyl-aminoethylphosphonic acid. The conversion can be effected by slurrying the N-carbobenzoxy-β-alanyl-aminoethylphosphonic acid in glacial AcOH. To the mixture, HBr in AcOH (30 wt %) is added. The reaction can be heated and allowed to mix for a period of not less than 1 hour. The product can be isolated by usual workup and precipitation.

EXAMPLE XI

β-alethine Combined with Melphalan MOPC-315 Myeloma

Published studies with the slow-growing, relatively non-aggressive NS-1 myeloma (Cancer Research, 1994, 54: 5636–5642) showed that β-alethine (BT) was 100% effective in causing NS-1 inoculated animals to survive. In this series of experiments, the effect of BT alone or in combination with melphalan (mp) was tested in Balb/c mice against the more aggressive MOPC-315 myeloma which grows from 1 million cells to 2 cm in 10 days and kills at a rate of nearly 100% in another 10 days if not treated. A suboptimal dose of 1.25 mg/kg melphalan was chosen for this study because it was expected to cure about half of the animals. The amount of β-alethine varied from study to study, but the amount of melphalan remained constant.

In six separate studies mice were treated with the chemotherapeutic agent melphalan (mp), BT alone, BT and mp, or vehicle, following s.c. administration to the host mouse of myeloma cells, either 1 million cells (high tumor burden) or $3 \times 10^5$ cells (low tumor burden). There were ten mice in each group. All drugs were injected i.p. Date of death and tumor size or complete disappearance of tumor were monitored. In this model, it is accepted that disappearance of tumor correlates positively with long term cure. Table 6 presents survival data for all six studies.

TABLE 6

MOPC-315 Myeloma - Survival Study

| Dose per kg | | | | | | | | Animals Surviving on Each Test Day | | | | | | | | | | |
|---|---|---|---|---|---|---|---|---|---|---|---|---|---|---|---|---|---|---|
| day: | 10 | 11 | 12 | 13 | 14 | 15 | 16 | 17 | 18 | 19 | 20 | 21 | 22 | 23 | 24 | 26 | 27 | 29 | 31 |

1 β-alethine ip day 2 (1 × 10⁶ tumor cells)

| | | 10 | 11 | 12 | 13 | 14 | 15 | 16 | 17 | 18 | 19 | 20 | 21 | 22 | 23 | 24 | 26 | 27 | 29 | 31 |
|---|---|---|---|---|---|---|---|---|---|---|---|---|---|---|---|---|---|---|---|---|
| Vehicle | | 10 | 10 | 10 | 9 | 7 | 5 | 5 | 4 | 3 | 3 | 1 | 1 | 1 | 1 | 0 | | | | |
| BT | 30 fg | 10 | 10 | 10 | 8 | 5 | 3 | 3 | 3 | 2 | 2 | 0 | 0 | | | | | | | |
| Alone | 3 ng | 10 | 10 | 10 | 9 | 8 | 7 | 6 | 4 | 3 | 3 | 2 | 0 | | | | | | | |
| | 100 µg | 10 | 10 | 10 | 10 | 7 | 6 | 6 | 5 | 3 | 3 | 1 | 0 | | | | | | | |
| | 3 mg | 10 | 10 | 10 | 10 | 7 | 4 | 4 | 3 | 2 | 2 | 1 | 1 | 1 | 1 | 0 | | | | |

| Dose per kg | | | | | | | | Animals Surviving on Each Test Day | | | | | | | | | | |
|---|---|---|---|---|---|---|---|---|---|---|---|---|---|---|---|---|---|---|
| day | 10 | 11 | 12 | 13 | 14 | 15 | 16 | 17 | 18 | 19 | 20 | 21 | 22 | 23 | 25 | 26 | 27 | 29 | 31 |

2 β-alethine ip day 10 (1 × 10⁶ tumor cells)

| | | 10 | 11 | 12 | 13 | 14 | 15 | 16 | 17 | 18 | 19 | 20 | 21 | 22 | 23 | 25 | 26 | 27 | 29 | 31 |
|---|---|---|---|---|---|---|---|---|---|---|---|---|---|---|---|---|---|---|---|---|
| Vehicle | | 10 | 10 | 7 | 7 | 5 | 4 | 4 | 2 | 0 | | | | | | | | | | |
| BT | 30 fg | 10 | 10 | 9 | 7 | 5 | 5 | 1 | 1 | 0 | | | | | | | | | | |
| Alone | 3 ng | 10 | 10 | 10 | 10 | 7 | 5 | 5 | 4 | 1 | 1 | 1 | 0 | | | | | | | |
| | 100 µg | 10 | 9 | 6 | 5 | 5 | 5 | 4 | 4 | 1 | 1 | 0 | | | | | | | | |
| | 3 mg | 10 | 9 | 6 | 5 | 5 | 5 | 4 | 4 | 1 | 1 | 0 | | | | | | | | |

| Dose per kg | | | | | | | | Animals Surviving on Each Test Day | | | | | | | | | | |
|---|---|---|---|---|---|---|---|---|---|---|---|---|---|---|---|---|---|---|
| day | 10 | 11 | 12 | 13 | 14 | 15 | 16 | 17 | 18 | 19 | 20 | 21 | 22 | 23 | 25 | 26 | 27 | 29 | 31 |

3 β-alethine ip day 0 (3 × 10⁵ tumor cells)

| | | 10 | 11 | 12 | 13 | 14 | 15 | 16 | 17 | 18 | 19 | 20 | 21 | 22 | 23 | 25 | 26 | 27 | 29 | 31 |
|---|---|---|---|---|---|---|---|---|---|---|---|---|---|---|---|---|---|---|---|---|
| Vehicle | | 10 | 10 | 10 | 10 | 6 | 6 | 3 | 0 | | | | | | | | | | | |
| BT | 100 ng | 10 | 10 | 10 | 10 | 7 | 7 | 4 | 0 | | | | | | | | | | | |
| Alone | 3 µg | 10 | 10 | 9 | 9 | 9 | 9 | 4 | 0 | | | | | | | | | | | |
| | 100 µg | 10 | 10 | 10 | 10 | 8 | 8 | 3 | 2 | 0 | | | | | | | | | | |
| | 3 mg | 10 | 10 | 10 | 10 | 10 | 10 | 8 | 3 | 3 | 0 | | | | | | | | | |

| Dose per kg | | | | | | | | Animals Surviving on Each Test Day | | | | | | | | | | |
|---|---|---|---|---|---|---|---|---|---|---|---|---|---|---|---|---|---|---|
| day | 10 | 11 | 12 | 13 | 14 | 15 | 16 | 17 | 18 | 19 | 20 | 21 | 22 | 23 | 25 | 26 | 27 | 29 | 31 |

4 Melphalan + β-alethine ip day 10 (1 × 10⁶ tumor cells)

| | | 10 | 11 | 12 | 13 | 14 | 15 | 16 | 17 | 18 | 19 | 20 | 21 | 22 | 23 | 25 | 26 | 27 | 29 | 31 |
|---|---|---|---|---|---|---|---|---|---|---|---|---|---|---|---|---|---|---|---|---|
| Vehicle | | 10 | 10 | 7 | 7 | 5 | 4 | 4 | 2 | 0 | | | | | | | | | | |
| mp | 1.25 mg | 10 | 8 | 5 | 4 | 3 | 3 | 3 | 3 | 3 | 3 | 3 | 3 | 3 | 3 | 3 | 3 | 3 | 3 | 1 |
| mp + BT | 30 fg | 10 | 10 | 9 | 9 | 9 | 9 | 8 | 7 | 6 | 6 | 3 | 1 | 1 | 1 | 1 | 1 | 1 | 1 | 1 |
| | 3 ng | 10 | 10 | 8 | 7 | 7 | 7 | 7 | 6 | 6 | 6 | 4 | 4 | 3 | 3 | 3 | 3 | 3 | 3 | 3 |
| | 100 µg | 10 | 9 | 9 | 9 | 9 | 9 | 8 | 7 | 7 | 7 | 6 | 5 | 4 | 4 | 4 | 4 | 4 | 4 | 4 |
| | 3 mg | 10 | 10 | 9 | 9 | 9 | 9 | 8 | 8 | 8 | 8 | 7 | 5 | 5 | 5 | 5 | 5 | 5 | 5 | 5 |

| Dose per kg | | | | | | | | Animals Surviving on Each Test Day | | | | | | | | | | |
|---|---|---|---|---|---|---|---|---|---|---|---|---|---|---|---|---|---|---|
| day | 10 | 11 | 12 | 13 | 14 | 15 | 16 | 17 | 18 | 19 | 20 | 21 | 22 | 23 | 25 | 26 | 28 | 29 | 31 |

5 Melphalan (mp) + β-alethine ip day 9 (1 × 10⁶ tumor cells)

| | | 10 | 11 | 12 | 13 | 14 | 15 | 16 | 17 | 18 | 19 | 20 | 21 | 22 | 23 | 25 | 26 | 28 | 29 | 31 |
|---|---|---|---|---|---|---|---|---|---|---|---|---|---|---|---|---|---|---|---|---|
| mp | 1.25 mg | 10 | 10 | 10 | 10 | 10 | 10 | 10 | 10 | 10 | 10 | 9 | 9 | 9 | 8 | 8 | 8 | 7 | 7 | 7 |
| mp + BT | 100 µg | 10 | 10 | 10 | 10 | 10 | 10 | 10 | 10 | 10 | 8 | 8 | 8 | 8 | 8 | 8 | 7 | 7 | 7 | |
| | 1 mg | 10 | 10 | 10 | 10 | 10 | 10 | 10 | 10 | 10 | 10 | 10 | 10 | 10 | 10 | 10 | 10 | 10 | 10 | |
| | 10 mg | 10 | 10 | 10 | 10 | 10 | 10 | 10 | 10 | 10 | 10 | 10 | 10 | 10 | 10 | 10 | 9 | 9 | 9 | |
| | 100 mg | 9* | 9 | 9 | 9 | 9 | 9 | 9 | 9 | 9 | 9 | 9 | 9 | 9 | 9 | 9 | 9 | 9 | 9 | |

| Dose per kg | | | | | | | | Animals Surviving on Each Test Day | | | | | | | | | | |
|---|---|---|---|---|---|---|---|---|---|---|---|---|---|---|---|---|---|---|
| day | 10 | 11 | 12 | 13 | 14 | 15 | 16 | 17 | 18 | 19 | 20 | 21 | 22 | 23 | 25 | 26 | 27 | 29 | 31 |

6 β-alethine ip starting day 9, 10 or 11; 75 mg/kg mp ip day 10. (1 × 10⁶ tumor cells)

| | | 10 | 11 | 12 | 13 | 14 | 15 | 16 | 17 | 18 | 19 | 20 | 21 | 22 | 23 | 25 | 26 | 27 | 29 | 31 |
|---|---|---|---|---|---|---|---|---|---|---|---|---|---|---|---|---|---|---|---|---|
| mp d 10 | 1.25 mg | 20 | 20 | 20 | 20 | 20 | 20 | 19 | 19 | 19 | 19 | 19 | 15 | 9 | 9 | 7 | 4 | 3 | 2 | 2 |
| mp + BT | | | | | | | | | | | | | | | | | | | | |
| day 9 | 75 mg | 10 | 10 | 10 | 10 | 10 | 10 | 10 | 10 | 9 | 9 | 9 | 5 | 5 | 3 | 2 | 2 | 1 | 1 | |
| day 10 | 75 mg | 10 | 10 | 10 | 10 | 10 | 10 | 9 | 9 | 9 | 8 | 8 | 7 | 7 | 7 | 5 | 4 | 3 | 2 | |
| day 11 | 75 mg | 10 | 10 | 10 | 10 | 9 | 9 | 7 | 7 | 7 | 5 | 5 | 5 | 4 | 3 | 2 | 1 | 1 | 1 | |

*In Study #5, in the 100 mg group, one of the 10 mice died for reasons unknown and it not included in the analysis.

Effects of β-alethine Alone on High Tumor Burden Animals

Studies #1–3 tested β-alethine given alone.

In the first two studies [Table 6, #1 & 2], BT was administered to high tumor burden animals that had been injected with 1 million melanoma cells. BT administered to groups of 8 mice each at doses of 30 femtograms/kg to 3 milligrams/kg on day 2 or day 10 after myeloma cell injection had no effect on survival when administered to these high tumor burden animals.

In a third study, BT (0.1 mg to 3 mg/kg) was administered alone to animals with a lower tumor burden. In this experiment, BT was injected simultaneously with a lower dose of melanoma cells ($3\times10^5$ cells). Only the highest dose of BT (3 mg/kg) significantly increased length of survival (survival analysis p=0.007) in these animals. The results in Table 6, #3 show that 3 mg/kg beta-alethine prolonged survival from 16 days in control animals, to 18 days. This difference is meaningful given the generally rapid fatality in the murine MOPC-315 model.

Effects of the Combination BT and Melphalan on High Tumor Burden Animals

Three additional studies [4–6] tested the anticancer effects of different doses of BT in combination with 1.25 mg/kg melphalan against mice having received a high tumor burden of 1 million cells. One injection of B-alethine was given; amounts ranged from 30 fg/kg to 100 mg/kg.

In the first of the three studies (#4), treatment was initiated 10 days after myeloma cell injection into the host. The doses of BT were 30 fg/kg to 3 mg/kg. Mp was only given at a dose of 1.25 mg/kg, which is a sub-optimal dose expected to cure up to half of the animals. All drugs were given on day 10.

In study #4, survival was increased in the groups receiving combination therapy at three doses of BT, relative to controls having no drugs at all, and to the group receiving melphalan only. The highest dose of 3 mg/kg BT was the most effective. The difference in survival between 3 mg/kg BT with 1.25 mg/kg mp, and mp alone, was statistically significant (survival analysis p=0.03). The first occurrence of cure was observed 11 days after treatment when BT (3 mg/kg) was administered together with melphalan; five of the ten mice in this group were completely cured by day 16. The cured animals remained tumor-free for over 50 days and survived without recurrence even when challenged with additional myeloma cells. Four animals survived in the group receiving 100 ug/kg BT with the mp. By contrast, only one animal in ten was cured by melphalan alone, and this cure occurred 19 days after treatment began. The addition of 3 mg/kg BT to melphalan dramatically increased the number of apparent cures five-fold over melphalan alone. Further, the combination drug also decreased the time to cure and the number of deaths. Thus, adding BT to melphalan produced a synergistic anticancer effect that was much greater than the anticipated additive effects of these compounds. Beta-alethine alone even at a very high dose, was ineffective in treating animals having a high tumor burden (see Study #2 above). Studies #2 and #4 were parallel and used the same control group.

Table 7 compares tumor size in groups receiving the highest BT dose (3 mg/kg) either alone or with mp in these two studies. Melphalan alone had only one fifth the cures observed with the combination, and displayed a longer time before the first cure was observed than with the combination drug.

TABLE 7

Mean Tumor Size (in mm) in 2 Studies Treating on Day 10

| | | day 10 | day 14 | day 17 | day 21 | day 29 |
|---|---|---|---|---|---|---|
| #2 BETATHINE as Single Agent Therapy | 3 mg BT alone | 21.5 | 24 | 24 | (dead) | |
| | saline | 20 | 25 | 26 | (dead) | |
| #4 Combination Therapy | mp & 3 mg BT | 23 | 22 | 15.5 | 12 | 0 |
| | mp alone | 22.5 | 19 | 17 | 22 | 28 |

Since a dose-response relationship was observed in #4, higher doses of BT (0.1, 1, 10 and 100 mg/kg BT) were administered with or without mp in study #5. Treatment was also started one day earlier, i.e. on day 9. Most mice survived and were cured in all groups. All the mice (either 9 or 10 per group) survived when given the combination having either 1 or 100 mg/kg BT. At 10 mg/kg BT with mp, 9 of 10 survived. By contrast, only 7 of 10 survived in the control group receiving 1.25 mg/kg mp alone (p=0.08 for survival difference). Although there were relatively good responses to all therapies, the tumors regressed more quickly (based on tumor size) in the 100 mg/kg BT/mp combination group. Due to the small sample size, this difference was significant only on day 16 (p=0.05). The tumor sizes are presented in Table 8.

TABLE 8

Effect of Beta-alethine and Melphalan on MOPC-315 Myeloma Tumor Size (mm): Treatment on Day 9

| day after tumor inoculation | 13 | 16 | 20 | 23 | 27 |
|---|---|---|---|---|---|
| 1.25 mg/kg mp | | 20.4 | 19.2 | 17.0 | 10.2 | 0 |
| 100 mg/kg BT & 1.25 mg/kg m | 18.6 | 15.0 | 12.9 | 6.4 | 0 |

In the third study with the combination [#6], all tumors grew unusually rapidly and no therapy was effective for most animals, however, there was a small advantage in the groups receiving BT on the same day as the melphalan. All groups received 1.25 mg/kg mp on day 10, 75 mg/kg BT was administered on day 9, 10 or 11, i.e, 1 day prior to mp (day 9), the same day (day 10), or the following day (day 11). There were 10 animals in each combination group and 20 in the mp-only group. Despite the rapid tumor growth, a decreased tumor size (21 vs. 26 mm) and an increased cure rate (2/10 vs. 2/20) were seen in the group receiving combination therapy where BT and mp were given on the same day (day 10), compared to melphalan alone; however, these results were not statistically significant. (See Table 9.) Overall in this third study, BT was able to improve the effects of melphalan, even when the tumor was so aggressive that all therapies were inadequate. Further, the addition of beta-alethine to mp permitted an optimal effect at what are clinically suboptimal doses of mp if mp were administered alone. This means that the amounts of mp can be reduced thereby decreasing toxicity effects associated with mp without sacrificing clinical efficacy.

TABLE 9

Deaths and Tumor Size (mm) in Mopc-315 Myeloma Treated with Combination of mp on Day 10 and BT on Day 9, 10, or 11

| mp on day 10 + BT on: | prior day (9) | same (10) | next (11) | none |
|---|---|---|---|---|
| day 21 tumor size (mm) | 27.7 | 21 | 26.2 | 25.8 |
| number in group | 10 | 10 | 10 | 20 |
| deaths day 21 | 1 | 2 | 5 | 5 |
| cures day 21 | 1 | 2 | 1 | 2 |
| day half are dead | 22 | 25 | 20 | 22 |

To summarize, these studies show that treatment with BT alone increases survival even with a highly aggressive myeloma if the tumor burden is relatively low, such as occurs in the early to moderate stages of myeloma. Unexpectedly, the combination of BT together with melphalan produced a synergistic anticancer effect over the effect observed with either BT or melphalan alone. The combination of BT/melphalan dramatically increased survival and total cures in a highly aggressive form of myeloma even when the tumor burden was high. Importantly, combination therapy prevented recurrence in cured animals even when challenged with a second injection of myeloma cells.

EXAMPLE XII

BT Produces a Synergism When Combined with Cyclophosphamide to Treat Melanoma

Eight female BDF1 mice, six to seven weeks old, were implanted in the foot on day 0 with an experimental skin cancer, B16 melanoma, that is extremely fast-growing and aggressive (solid melanoma). They were subsequently treated 2 days after implantation (day 2) with either a single s.c. injection of the alkylating agent cyclophosphamide (cp), a standard chemotherapeutic agent used in the treatment of melanoma, at a dose of 200 mg/kg, or a combination of BT/cp. The primary tumor was removed on day 17. (5 days after starting combination therapy) The size of the primary tumor and the presence of metastasis on day 42 was measured. Table 10 presents tumor size.

A statistically significant reduction of the size of primary tumor was observed on day 7 in animals treated with the combination of BT (30 mg/kg) 3× times a week starting on day 2 and cp (200 mg/kg) on day 1 compared to no treatment or cp alone. See Table 10. This reduction in tumor size persisted through day 17 when the experiment ended. Statistical significance of this difference was p=0.015 at day 17, measured using the Mann-Whitney U test. By contrast, 200 mg/kg cp alone did not significantly reduce the size of the primary tumor until day 10, and this reduction was temporary, lasting only until day 14. Further, the reduction in tumor size by 200 mg/kg mp was always much less than that caused by the combination.

The T/C ratio for medium tumor volume on day 17 was 52.5% for the combination and 82.3% for cp alone. (T/C is the ratio of the treatment value to the control value, where 100% is no difference. RTV is defined as the change in tumor volume from day 0, RTV can be used to calculate the T/C ratio). These findings indicate that BT greatly enhanced the anticancer properties of cyclophosphamide, producing an earlier, larger, and longer lasting effect on reducing the size of the primary tumor than cp alone.

TABLE 10

Primary Tumor Size (Median RTV) on B16 Melanoma:

|  | day 0 | 4 | 7 | 10 | 14 | 17 |
|---|---|---|---|---|---|---|
| Saline control | 1 | 1.0 | 2.7 | 6.8 | 17.9 | 36.9 |
| BT 30 mg/kg alone | 1 | 1.7 | 3.3 | 7.5 | 23.2 | 34.8 |
| BT 30 ug/kg alone | 1 | 1.0 | 1.3 | 5.5 | 16.6 | 30.4 |
| BT 30 ng/kg alone | 1 | 1.0 | 3.1 | 8.1 | 15.7 | 32.4 |
| BT 30 pg/kg alone | 1 | 1.0 | 1.8 | 6.0 | 17.3 | 62.0 |
| BT 30 fg/kg alone | 1 | 1.7 | 2.4 | 7.0 | 16.1 | 41.6 |
| cp 200 mg BT 30 mg | 1 | 1.0 | 1.1 | 2.3 | 7.5 | 19.4 |
| cp 200 mg/kg alone | 1 | 1.0 | 2.4 | 3.5 | 12.9 | 32.6 |

TABLE 11

Statistically Significant Effect on Reducing Tumor Volume

| TREATMENT | DAY 7 | DAY 10 | DAY 14 | DAY 17 |
|---|---|---|---|---|
| Cyclophosphamide (cp) | No | Yes | Yes | No |
| Cp + BT | Yes | Yes | Yes | Yes |

The combination of BT/cp also drastically reduced metastases in these animals. The number and site of metastases in these animals, measured at autopsy, were recorded for each animal. As seen in Tables 12 and 13, the control group receiving cp alone had dozens of metastatic lesions in the lungs and frequently had cancer in other organs. By contrast, combination therapy with 30 mg/kg BT and 200 mg/kg cp resulted in fewer and smaller lung metastases (p=0.08). Further, no metastasis to organs other than the lungs was observed with combination therapy. Thus, the combination of BT/cp helped control the spread of the primary tumor to a greater degree than did cp alone. None of the animals treated with the combination had greater than 10 metastatic lesions, while two-thirds of untreated controls and half of the Cp-treated animals had 10 or more metastatic lesions.

TABLE 12

Beta-alethine plus cp Effect on Metastasis
Percent of Animals with Greater than 10 Metastases

| Control | 66.7 |
|---|---|
| Cp 200 mg/kg | 50 |
| Cp 200 mg/kg + BT 30 mg/kg | 0 |

TABLE 13

Number of Metastases on Day 42

| Number of Metastases | 0–10 | 11–20 | 21–30 | over 30 (full of metastases) |
|---|---|---|---|---|
| Saline | 5 | 3 | 2 | 5 |
| Cp 200 mg/kg | 4 | 3 | 0 | 1 |
| Cp 200 mg/kg and BT 30 mg/kg | 10 | 0 | 0 | 0 |

EXAMPLE XIII

Beta-alethine and Cyclophosphamide in MT-1 Breast Cancer

β-alethine was evaluated in a breast cancer xenograft model (MT-1) in male nude mice in four experiments. Fragments of tumor, 3–4 mm in diameter were subcutaneously inoculated. In the first experiment, BT (30 fg/kg to 30 mg/kg) was administered alone via intra-peritoneal (i.p.) injection either 3× week or on days 13, 27 and 41 after subcutaneous tumor inoculation. Animals were observed over a period of 45 days after tumor cell injection. Injection of BT at a dose of 30 ng/kg injected every 14 days produced a tumor growth inhibition comparable to or greater than that achieved in previous studies with known clinical cytostatics including mitoxantrone and cyclophosphamide, and greater than those for optimal doses of doxorubicin, vincristine, 5-fluorouracil, tamoxifen, and cisplatin. (Fichtner, I et al, in Arnold, W, et al. (Eds.), *Immunodeficient Animals: Models for Cancer Research.* Contrib. Oncology, Basel, Karger, 1996, volume 51; Naundorf, H, et al., *Breast Cancer Research and Treatment*, 23, 87–95, 1992.) Importantly, treatment with BT did not produce any toxic effects as could be measured by changes in body weight or blood parameters.

Statistically significant differences were observed within one week of a single injection of BT, and increased throughout the experiment. (At day 45, for the Mann-Whitney U test, p=0.003.) As seen in Table 14, tumors in all groups started at about 0.1 cm$^3$. By day 38, control tumors were almost 2 cm$^3$ and they reached almost 3 cm$^3$ by day 45. In contrast, the optimally treated BT group receiving 30 ng/kg never exceeded the 0.4 cm$^3$ size reached on day 38. Injecting every other week was more effective than administering the same dose 3× week. The T/C ratio (treated vs. control median relative tumor volume) was 29% at 45 days following 3 injections of 30 ng/kg BT.

TABLE 14

Median Tumor Size (cm$^3$) in MT-1 Breast Cancer Study BT Treatment Every 14 days

| per kg | day 13 | 16 | 20 | 23 | 27 | 30 | 34 | 38 | 41 | 45 |
|---|---|---|---|---|---|---|---|---|---|---|
| Saline | 0.106 | 0.192 | 0.385 | 0.566 | 0.839 | 1.070 | 1.588 | 1.875 | 2.303 | 2.902 |
| 30 ug | 0.055 | 0.095 | 0.180 | 0.193 | 0.325 | 0.408 | 0.410 | 0.607 | 0.696 | 0.743 |
| 30 ng | 0.080 | 0.104 | 0.176 | 0.202 | 0.250 | 0.294 | 0.298 | 0.426 | 0.429 | 0.419 |
| 30 fg | 0.104 | 0.128 | 0.213 | 0.253 | 0.442 | 0.637 | 1.062 | 1.241 | 1.464 | 1.911 |

TABLE 15

RTV in MT-1 Breast Cancer Study

| | day 13 | 16 | 20 | 23 | 27 | 30 | 34 | 38 | 41 | 45 |
|---|---|---|---|---|---|---|---|---|---|---|
| Saline | 1 | 1.7 | 3.7 | 4.9 | 7.0 | 8.1 | 12.5 | 13.9 | 17.7 | 20.7 |
| 30 ug | 1 | 1.4 | 2.6 | 3.0 | 4.3 | 5.2 | 6.0 | 9.1 | 11.5 | 14.0 |
| 30 ng | 1 | 1.4 | 2.1 | 2.3 | 2.8 | 3.4 | 3.8 | 4.5 | 4.9 | 6.0 |
| 30 fg | 1 | 1.6 | 3.4 | 4.4 | 7.6 | 9.3 | 11.9 | 16.1 | 18.2 | 19.8 |

In the second experiment with MT-1 breast cancer, BT was administered on day three only, at doses of 30 fg/kg to 3 micrograms/kg. The T/C ratio of treated vs. control median RTV was measured on day 28. RTV in the group receiving 3 ug/kg BT was 32%; for 300 ng/kg BT, the T/C ratio was 42%. The most effective dose of BT was 3 ug/kg which is a higher dose than was required in the first experiment. The other doses of BT (30 ng, 3 ng, 0.3 ng, and 0.03 ng) alone were not effective in this experiment. See Table 16. These observations of RTV were made only through day 28.

TABLE 16

Median RTV for MT-1 Tumors Treated with BT on Day 3

| day: | 8 | 14 | 21 | 28 |
|---|---|---|---|---|
| saline | 1.160 | 2.333 | 5.721 | 7.908 |
| 300 ng/kg | 1.105 | 1.243 | 2.532 | 3.317 |
| 3 ug/kg | 1.012 | 0.955 | 1.756 | 2.526 |

In a parallel experiment, a low dose of 30 ng of BT was injected directly into the tumor on days 3, 17 and 31. The T/C for RTV measured on day 35 was 50%.

TABLE 17

Median RTV for MT-1 Tumors Treated on Day 3 by Intratumor injection

| day | 8 | 11 | 14 | 17 | 21 | 24 | 28 | 31 | 35 |
|---|---|---|---|---|---|---|---|---|---|
| Saline | 1.29 | 1.66 | 2.35 | 3.35 | 6.11 | 8.22 | 10.01 | 13.43 | 17.79 |
| BT 30 ng | 1.27 | 1.40 | 1.77 | 2.61 | 3.74 | 4.34 | 4.93 | 6.37 | 8.01 |

In the fourth experiment, animals with advanced (day 42) tumors were given cp at doses of 300, 200 or 100 mg/kg, with or without 30 mg/kg BT (a single dose of BT was administered 30 minutes prior to cp). Beta-alethine given alone was not effective. At the lowest dose of 100 mg/kg, BT significantly improved the anti-tumor effect over an equivalent dose of cp alone as was measured by median tumor volume. Thus, the combination of BT/cp has a synergistic effect on treating breast cancer.

TABLE 18

BT/cp Combination Study on Advanced MT-1 Breast Cancer

A. Median Relative Tumor Volume

| | day 42 | 46 | 49 | 53 | 59 |
|---|---|---|---|---|---|
| Saline | 1 | 1.30 | 1.77 | 1.89 | 2.29 |
| 300 mg/kg cp | 1 | 1.34 | 1.14 | 1.15 | 1.14 |
| 200 mg/kg cp | 1 | 1.15 | 1.11 | 1.21 | 1.15 |
| 100 mg/kg cp | 1 | 1.37 | 1.54 | 1.50 | 1.85 |
| 30 mg/kg BT & 300 mg/kg cp | 1 | 1.12 | 1.29 | 1.19 | 0.95 |
| 30 mg/kg BT & 200 mg/kg cp | 1 | 1.30 | 1.30 | 1.25 | 0.99 |
| 30 mg/kg BT & 100 mg/kg cp | 1 | 1.16 | 1.17 | 1.13 | 1.85 |

B. Tumor Size, Body Weight and Blood Parameters

| | Dose | Δ weight, d 42–49 | T/C RTV d 49 | T/C RTV d 59 | WBC d 46 ($10^6$/mL) | Thrombocytes ($10^6$/mL) d 46 |
|---|---|---|---|---|---|---|
| control | | 0% | | | 16.0 | 765 |
| BT | 30 mg/kg | 0.01 | 72% | 165% | 14.4 | 789 |

TABLE 18-continued

BT/cp Combination Study on Advanced MT-1 Breast Cancer

| Cp + | 100 mg/kg | −7%  | 87% | 81% | 10.3 | 756 |
| BT   | 30 mg/kg  | 6%   | 66% | 81% | 8.5  | 774 |
| Cp + | 200 mg/kg | −18% | 63% | 50% | 5.5  | 505 |
| BT   | 30 mg/kg  | 10%  | 74% | 43% | 5.9  | 604 |
| Cp + | 300 mg/kg | −20% | 65% | 50% | 5.6  | 425 |
| BT   | 30 mg/kg  | −16% | 73% | 42% | 1.5  | 949 |

Table 19 shows data from a study in which eight animals having advanced tumors received 300 mg/kg cp with 30 mg/kg BT and eight animals received 300 mg/kg cyclophosphamide alone. A dose of 300 mg/kg exceeds the maximum tolerated dose (MTD). The cp-only group experienced 25% toxic deaths, while the group receiving the combination drug of the present invention had 0% toxic deaths. Thus, the addition of 30 mg/kg BT to a highly toxic dose of 300 mg/kg cyclophosphamide completely eliminated the toxic deaths caused by cyclophosphamide alone. Frequently, the effective dose of a chemotherapeutic agent approaches the toxic dose, therefore, there is a great need for a way to reduce toxicity without reducing the therapeutic effectiveness of the chemotherapeutic agent. Adding BT to a highly toxic dose of a chemotherapeutic agent provides a safety margin by reducing the toxicity of the agent.

Most tumors grew in size in the group receiving 300 mg of cp alone, indicating progression of the disease. Median tumor size increased 25%. By contrast, there was a 14% decrease in median tumor size in the BT/cp groups, and no progression of the disease. The increase in tumor size was statistically significant (chi-square p value for tumor regression=0.04, 1-tailed). Finally, the last two readings in the BT/cp group indicated tumor regression in 75% of the animals while only 12% showed regression in the Cp-only group.

TABLE 19

MT-1 Human Breast Cancer
BT Increases Tumor Regression and Decreases Toxic Deaths
Status of Individual Mice at Final Two Tumor Readings

| Status | Cp 300 mg/kg | Cp 300 mg/kg & BT 30 mg/kg |
|---|---|---|
| Died of toxic effects | 25% | 0% |
| Last 2 readings indicate progression | 12% | 0% |
| Last reading indicates progression | 25% | 0% |
| Last 2 readings stayed the same | 0% | 12% |
| Last reading indicates regression | 25% | 12% |
| Last 2 readings indicate regression | 12% | 75% |
| Group median tumor size change (measured on day 17) | increase 25% | decrease 14% |

Table 19 is based on change at last two readings (difference from day 7 to day 11 and from day 11 to day 17). When the last two readings are different, the final reading is used. The categories are mutually exclusive and include all 8 mice in each group. Values were rounded to two decimal places.

EXAMPLE IV

Beta-alethine Reduces the Toxicity of Taxol

The effect of combining BT with paclitaxel (PAC, or TAXOL™) on the toxicity of paclitaxel was investigated. In a first study, groups of 10 female non-tumor-bearing athymic (NCr-nu) mice were administered paclitaxel i.v. at doses of 50 and 30 mg/kg/dose on a qldx5 schedule, which means once each day for five days. Paclitaxel (PAC) was in 12.5% cremophor/12.5% ethanol/75% saline alone, or in combination with 30 mg/kg BT (first dissolved in saline) and delivered as a single i.v. injection (0.1 cc/10 gm body weight). BT was also administered on a qldx5 schedule. Body weights were measured twice a week and survival data was recorded daily. The study was terminated on day 21.

The results, summarized in Table 20 below, show that less weight was lost in the group receiving 50 mg PAC/30mg BT at all time points, and there was an increase in weight gain on day 21 that is twice the increase with PAC alone. The addition of BT to 30 mg PAC decreased the amount of weight lost by days 7 and 10, but did not increase weight on days 14 and 21 over levels observed with 30 mg PAC alone. Weight loss values reflect the lowest recorded weight, which was on day 7 for all groups. Importantly, there were fewer deaths when BT was coadministered with either 30 mg or 50 mg paclitaxel.

For the group receiving 50 mg paclitaxel, the survival difference was statistically significant (log rank=6.41, p=0.0113). There were 9 deaths on day 21 with 50 mg PAC alone, but only 2 deaths when 30 mg BT was administered with 50 mg PAC. When BT was coadministered with 30 mg PAC there was only 1 death on day 21, which was due not to toxicity, but to a technician error. By contrast, there were 2 toxic deaths with 30 mg PAC alone.

TABLE 21

Effect of the Combination β-alethine (BT)/paclitaxel (PAC)
On Mean Body Weight and Mortality

| Group | Outcome | Day 1 | 7 | 10 | 14 | 21 |
|---|---|---|---|---|---|---|
| PAC. 50 mg | mean weight (gm) | 19 | 13 | 12 | 14 | 21 |
| BT 0 mg | % weight change | — | −31.6 | −36.8 | −26.3 | +10.5 |
|  | deaths (cummul.) | 0 | 1 | 9 | 9 | 9 |
| PAC. 50 mg | mean weight (gm) | 19 | 14 | 17 | 19 | 23 |
| BT 30 mg | % weight change | — | −26.3 | −10.5 | 0 | +21.1 |
|  | deaths (cummul.) | 0 | 2 | 2 | 2 | 2 |
| PAC. 30 mg | mean weight | 19 | 14 | 15 | 18 | 23 |
| BT 0 mg | % weight change | — | −26.3 | −21.1 | −5.3 | +21.1 |
|  | deaths | 0 | 1 | 2 | 2 | 2 |
| PAC. 30 mg | mean weight | 19 | 16 | 19 | 20 | 23 |
| BT 30 mg | % weight change | — | −15.8 | 0 | +5.3 | +21.1 |
|  | deaths | 0 | 0 | 0 | 1* | 1* |

*due technician error that caused immediate death which was not due to toxicity which would have caused death after a delay of several days.

In the second study, groups of 10 female non-tumor-bearing athymic (NCr-nu) mice were administered PAC i.v. (40 mg/kg/dose) or dexamethasone i.p. (10 mg/kg/inj.) once a day for 5 days. PAC was in 10% cremophor/90% saline. PAC and dexamethasone were injected i.v. either alone or thirty minutes after administering either 30 or 100 mg/kg/doses BT (first dissolved in saline) injected i.p. Body weights were measured daily through day 14, then twice weekly through day 29 when the study was terminated. Deaths were also observed daily.

The results shown in Table 22 show greater recovery from PAC-induced weight loss when 30 mg/kg BT was coadministered with PAC. There was little weight loss with BT alone or in combination with dexamethasone, and no changes with dexamethasone alone. There were no toxic deaths in this study, however a total of 7 mice died due to an embolic reaction to the PAC injection in the BT combination groups.

TABLE 22

Percent Body Weight Loss* From Day 0

| | day 1 | 5 | 6 | 7 | 8 | 9 | 10 | 11 | 12 | 13 | 21 |
|---|---|---|---|---|---|---|---|---|---|---|---|
| saline | 2.7 | 4.6 | 5.2 | 6.9 | 4.8 | 5.7 | 5.1 | 7.4 | 4.6 | 3.9 | 2.6 |
| Taxol 40 mg/kg IV | 3.8 | 10.7 | 11.0 | 15.2 | 17.2 | 17.5 | 14.6 | 11.8 | 10.4 | 7.8 | −1.2 |
| BT 100 mg IP | 4.2 | 0.4 | 2.6 | 2.5 | 3.8 | 5.8 | 4.6 | 5.6 | 6.3 | 3.2 | 3.4 |
| BT 30 mg IP | 1.2 | 1.1 | −0.9 | 0.1 | 2.8 | 3.4 | 4.6 | 7.2 | 6.8 | 7.7 | 0.7 |
| Taxol & BT 100 mg/kg | 1.7 | 6.6 | 13.0 | 15.6 | 16.5 | 15.1 | 15.5 | 13.0 | 12.1 | 7.4 | −6.2 |
| Taxol & BT 30 mg/kg | 3.9 | 12.0 | 14.2 | 13.9 | 10.2 | 9.9 | 7.2 | 2.9 | 6.5 | 1.0 | −3.5 |
| DEX.10 mg IP | 3.0 | 4.6 | 2.8 | 3.4 | 2.4 | 3.6 | 2.8 | 1.3 | 3.7 | 2.1 | 0.1 |
| DEX.10 mg & BT 30 mg | 3.1 | 7.3 | 6.9 | 4.5 | 5.7 | 4.1 | 2.6 | 1.9 | −1.9 | −0.3 | −6.1 |

*weight gain indicated by negative numbers

Thus, two studies with different procedures showed similar beneficial effects of administering 30 mg/kg BT to decrease paclitaxel-induced toxicity.

All documents cited above are hereby incorporated in their entirety by reference. The entire contents of U.S. Provisional Appln. No. 60/005,336, filed Oct. 17, 1995; and Nos. 60/075,966 and 60/085,474, are also incorporated herein in their entirety.

One skilled in the art will appreciate from a reading of this disclosure that various changes in form and detail can be made without departing from the true scope of the invention.

What is claimed is:

1. A method of preventing, treating or delaying the clinical appearance of a neoplastic or pre-neoplastic condition sensitive to a synergistic combination comprising administering to an animal in need thereof a synergistically effective amount of beta-alethine and at least one anticancer agent selected from the group consisting of melphalan and cyclophosphamide.

2. A pharmaceutical composition, comprising a synergistically effective amount of beta-alethine and at least one anticancer agent selected from the group consisting of melphalan and cyclophosphamide.

* * * * *